United States Patent
Sawchuk

(10) Patent No.: US 11,638,828 B2
(45) Date of Patent: May 2, 2023

(54) DEMAND DRIVEN CAPACITOR CHARGING FOR CARDIAC PACING

(71) Applicant: Medtronic, Inc., Minneapolis, MN (US)

(72) Inventor: Robert T. Sawchuk, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 119 days.

(21) Appl. No.: 17/001,406

(22) Filed: Aug. 24, 2020

(65) Prior Publication Data

US 2020/0384268 A1    Dec. 10, 2020

Related U.S. Application Data

(62) Division of application No. 15/676,066, filed on Aug. 14, 2017, now Pat. No. 10,751,541.

(51) Int. Cl.
| | | |
|---|---|---|
| *A61N 1/368* | (2006.01) | |
| *A61N 1/37* | (2006.01) | |
| *A61N 1/39* | (2006.01) | |
| *A61N 1/362* | (2006.01) | |

(Continued)

(52) U.S. Cl.
CPC ......... *A61N 1/3684* (2013.01); *A61N 1/3621* (2013.01); *A61N 1/371* (2013.01); *A61N 1/3706* (2013.01); *A61N 1/3925* (2013.01); *A61N 1/3956* (2013.01); *A61N 1/3962* (2013.01);

(Continued)

(58) Field of Classification Search
CPC ................ A61N 1/3621; A61N 1/3956; A61N 1/39622; A61N 1/025; A61N 1/05; A61N 1/3712; A61N 1/37512; A61N 1/362; A61N 1/3706; A61N 1/365; A61N 1/3702; A61N 1/00; A61N 1/08; A61N 1/36; A61N 1/36178; A61N 1/37; A61B 5/686; A61B 5/4836; A61B 5/6869; A61B 5/0006; A61B 5/0031; A61B 5/04012; A61B 5/0245; A61B 5/04; A61B 5/0402; A61B 5/024; A61B 5/00; A61B 5/02; A61B 5/486

See application file for complete search history.

(56) References Cited

U.S. PATENT DOCUMENTS

| | | |
|---|---|---|
| 4,406,286 A | 9/1983 | Stein |
| 5,387,228 A | 2/1995 | Shelton |
| 5,447,522 A | 9/1995 | Chang et al. |

(Continued)

OTHER PUBLICATIONS (PCT/US2018/045934) PCT Notification of Transmittal of the International Search Report and the Written Opinion of the International Searching Authority, dated Aug. 9, 2018, 13 pages.

*Primary Examiner* — Deborah L Malamud

(57) ABSTRACT

An implantable medical device system delivers a pacing pulse to a patient's heart and starts a first pacing interval corresponding to a pacing rate in response to the delivered pacing pulse. The system charges a holding capacitor to a pacing voltage amplitude during the first pacing interval. The system detects an increased intrinsic heart rate that is at least a threshold rate faster than the current pacing rate from a cardiac electrical signal received by a sensing circuit of the implantable medical device. The system starts a second pacing interval in response to an intrinsic cardiac event sensed from the cardiac electrical signal and withholds charging of the holding capacitor for at least a portion of the second pacing interval in response to detecting the increased intrinsic heart rate.

25 Claims, 19 Drawing Sheets

(51) Int. Cl.
*A61N 1/05* (2006.01)
*A61N 1/365* (2006.01)

(52) U.S. Cl.
CPC .......... *A61N 1/0573* (2013.01); *A61N 1/3622* (2013.01); *A61N 1/36542* (2013.01)

(56) References Cited

U.S. PATENT DOCUMENTS

| | | |
|---|---|---|
| 6,283,985 B1 | 9/2001 | Harguth et al. |
| 6,353,760 B1 | 3/2002 | Lyden |
| 6,706,059 B2 | 3/2004 | Harguth et al. |
| 6,892,096 B2 | 5/2005 | Lyden |
| 7,002,790 B2 | 2/2006 | Hossick-Schott et al. |
| 7,027,865 B2 | 4/2006 | Erickson et al. |
| 7,131,988 B2 | 11/2006 | Harguth et al. |
| 7,212,856 B2 | 5/2007 | Rossing |
| 7,544,218 B2 | 6/2009 | Norton et al. |
| 7,570,995 B1 | 8/2009 | Kroll et al. |
| 7,761,150 B2 | 7/2010 | Ghanem et al. |
| 8,195,291 B2 | 6/2012 | Norton et al. |
| 9,579,512 B2 | 2/2017 | Demmer |
| 2003/0204222 A1 | 10/2003 | Leinders et al. |
| 2004/0215260 A1 | 10/2004 | Vonk et al. |
| 2005/0182389 A1 | 8/2005 | LaPorte et al. |
| 2006/0167503 A1 | 7/2006 | Warren et al. |
| 2007/0156189 A1 | 7/2007 | DeGroot et al. |
| 2012/0283795 A1 | 11/2012 | Stancer et al. |
| 2015/0306375 A1 | 10/2015 | Marshall et al. |
| 2015/0306410 A1 | 10/2015 | Marshall et al. |
| 2015/0306475 A1 | 10/2015 | Curtis et al. |
| 2016/0158567 A1 | 6/2016 | Marshall et al. |
| 2016/0228708 A1 | 8/2016 | Ternes et al. |
| 2016/0228718 A1 | 8/2016 | Koop |
| 2016/0279425 A1 | 9/2016 | Demmer |
| 2017/0157399 A1 | 6/2017 | Anderson et al. |
| 2017/0157412 A1 | 6/2017 | Nikolski et al. |
| 2017/0157413 A1 | 6/2017 | Anderson et al. |

# DEMAND DRIVEN CAPACITOR CHARGING FOR CARDIAC PACING

RELATED APPLICATION

This application is a Division of U.S. patent application Ser. No. 15/676,066, filed Aug. 14, 2017, the content of both of which is incorporated herein by reference in its entirety.

TECHNICAL FIELD

The disclosure relates generally to an implantable medical device (IMD) system and method that delivers cardiac pacing pulses and particularly to an IMD system and method for controlling the charging of capacitors used for generating and delivering cardiac pacing pulses based on pacing demand.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include cardiac pacing pulses or cardioversion/defibrillation (CV/DF) shocks.

The medical device may sense cardiac electrical events attendant to the intrinsic heart activity for detecting an abnormal intrinsic heart rhythm. Upon detection of an abnormal rhythm, such as bradycardia, tachycardia or fibrillation, an appropriate electrical stimulation therapy may be delivered to restore or maintain a more normal rhythm of the heart. For example, an ICD may deliver pacing pulses to the heart of the patient upon detecting bradycardia or tachycardia or deliver CV/DF shocks to the heart upon detecting tachycardia or fibrillation.

The ICD may sense the cardiac electrical signals from a heart chamber and deliver electrical stimulation therapies to the heart chamber using endocardial electrodes carried by transvenous medical electrical leads. In other cases, a non-transvenous lead may be coupled to the ICD, in which case the ICD may sense cardiac electrical signals and deliver electrical stimulation therapy to the heart using extra-cardiovascular electrodes. The energy of a therapeutic electrical stimulation pulse required to effectively stimulate the heart using the extra-cardiovascular electrodes is typically greater than the energy required to stimulate the heart using endocardial electrodes. A pacing circuit may include a holding capacitor that is charged to a pacing voltage amplitude for generating a pacing pulse according to the pacing pulse energy required to capture the pacing heart using the pacing electrode vector that is available.

SUMMARY

In general, the disclosure is directed to techniques for controlling charging of at least one holding capacitor that is used to deliver a cardiac electrical stimulation pulse by a therapy delivery circuit of an implantable medical device. An IMD operating according to these techniques may withhold capacitor charging when increased intrinsic heart rate criteria are satisfied. Charging of the capacitor may be withheld for at least a portion of a pacing interval, e.g., by charging after a delay interval has expired. The charging delay interval may be equal to, greater than or less than the pacing interval. In response to decreased heart rate criteria being satisfied, the IMD may switch back to charging the holding capacitor without delay, e.g., at the beginning or throughout a pacing interval as needed to maintain the holding capacitor charge at the pacing voltage amplitude in a ready state for delivering a pacing pulse. In some examples, the IMD may be configured to control when the function of switching between two different charging modes, e.g., a delayed capacitor charging mode and a capacitor charging without delay mode, is enabled (turned on) or disabled (turned off). When this charging mode switching function is disabled, the IMD may operate to charge the holding capacitor according to one, default charging mode. When the charging mode switching function is enabled, the IMD may operate to switch between two different charging modes based on intrinsic heart rate criteria and/or other pacing demand criteria.

In one example, the disclosure provides an IMD system including a therapy delivery circuit, a sensing circuit and a control circuit coupled to the therapy delivery circuit and the sensing circuit. The therapy delivery circuit has a holding capacitor and a charging circuit configured to charge the holding capacitor to a pacing voltage amplitude. The sensing circuit is configured to receive a cardiac electrical signal from a patient's heart. The control circuit is configured to control the therapy delivery circuit to deliver a pacing pulse, start a first pacing interval corresponding to a pacing rate in response to the delivered pacing pulse, control the therapy delivery circuit to charge the holding capacitor during the first pacing interval according to a first charging mode, detect an increased intrinsic heart rate from the cardiac electrical signal that is at least a threshold rate faster than the pacing rate, switch from the first charging mode to a second charging mode in response to detecting the increased intrinsic heart rate, start a second pacing interval in response to an intrinsic cardiac event sensed from the cardiac electrical signal, and control the therapy delivery circuit to withhold charging of the holding capacitor for at least a portion of the second pacing interval according to the second charging mode.

In another example, the disclosure provides a method including delivering a pacing pulse by a therapy delivery circuit having a holding capacitor and a charging circuit configured to the charge the holding capacitor to a pacing voltage amplitude and starting a first pacing interval corresponding to a pacing rate in response to the delivered pacing pulse. The method further includes charging the holding capacitor during the first pacing interval according to a first charging mode and detecting an increased intrinsic heart rate that is at least a threshold rate faster than the pacing rate from a cardiac electrical signal received by a sensing circuit, switching from the first charging mode to a second charging mode in response to detecting the increased intrinsic heart rate, starting a second pacing interval in response to a first intrinsic cardiac event sensed from the cardiac electrical signal; and withholding charging of the holding capacitor for at least a portion of the second pacing interval according to the second charging mode.

In another example, the disclosure provides a non-transitory, computer-readable storage medium comprising a set of instructions which, when executed by a control circuit of an implantable medical device, cause the device to deliver a pacing pulse by a therapy delivery circuit having a holding capacitor and a charging circuit configured to the charge the holding capacitor to a pacing voltage amplitude and start a first pacing interval corresponding to a pacing rate in response to the delivered pacing pulse. The instructions further cause the device to charge the holding capacitor during the first pacing interval according to a first charging mode, detect an increased intrinsic heart rate that is at least a threshold rate faster than the pacing rate from a cardiac electrical signal received by a sensing circuit, switch from the first charging mode to a second charging mode in response to detecting the increased intrinsic heart rate, start a second pacing interval in response to a first intrinsic cardiac event sensed from the cardiac electrical signal; and withhold charging of the holding capacitor for at least a portion of the second pacing interval according to the second charging mode.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for controlling charging of a holding capacitor in a therapy delivery circuit of a cardiac medical device or system. A holding capacitor, or a combination of holding capacitors, is generally charged by a charging circuit to a pacing voltage amplitude for generating and delivering a cardiac pacing pulse. The holding capacitor may be charged as needed at the beginning or throughout a pacing interval that is started immediately after a pacing pulse or sensed intrinsic cardiac event, such as an R-wave or P-wave. In this way, the holding capacitor is maintained at the pacing voltage amplitude in a ready state until a pacing timing interval expires. Maintaining the charge of a holding capacitor or combination of capacitors at the pacing voltage amplitude, however, consumes energy supplied by the power source of the IMD. The techniques disclosed herein may be used to conserve energy normally required to charge and maintain a holding capacitor in a ready state for delivering cardiac pacing pulses by withholding capacitor charging during at least a portion or all of a pacing interval when increased heart rate criteria are met and/or low pacing demand criteria are met.

In some examples, the cardiac medical device system implementing the techniques disclosed herein may be an extra-cardiovascular ICD system. As used herein, the term "extra-cardiovascular" refers to a position outside the blood vessels and heart of a patient. Implantable electrodes carried by extra-cardiovascular leads may be positioned extra-thoracically (outside the ribcage and sternum, e.g., subcutaneously) or intra-thoracically (beneath the ribcage or sternum, e.g., substernally) but generally not in intimate contact with myocardial tissue. The techniques disclosed herein for controlling capacitor charging may be applied to a therapy delivery circuit that is coupled to extra-cardiovascular electrodes and likely to require relatively higher pacing voltage amplitude and/or longer pulse widths than a cardiac medical device coupled to endocardial or epicardial electrodes.

As such, techniques disclosed herein are described in conjunction with an ICD and implantable medical lead carrying extra-cardiovascular electrodes, but aspects disclosed herein may be utilized in conjunction with other cardiac medical devices or systems. For example, the techniques for controlling capacitor charging as described in conjunction with the accompanying drawings may be implemented in any implantable or external medical device enabled for delivering cardiac electrical stimulation pulses, including implantable pacemakers or ICDs coupled to transvenous, pericardial or epicardial leads carrying sensing and therapy delivery electrodes; intra-cardiac or leadless pacemakers or ICDs having housing-based electrodes; or external or wearable pacemakers or defibrillators coupled to external, surface or skin electrodes.

Figure 1A:
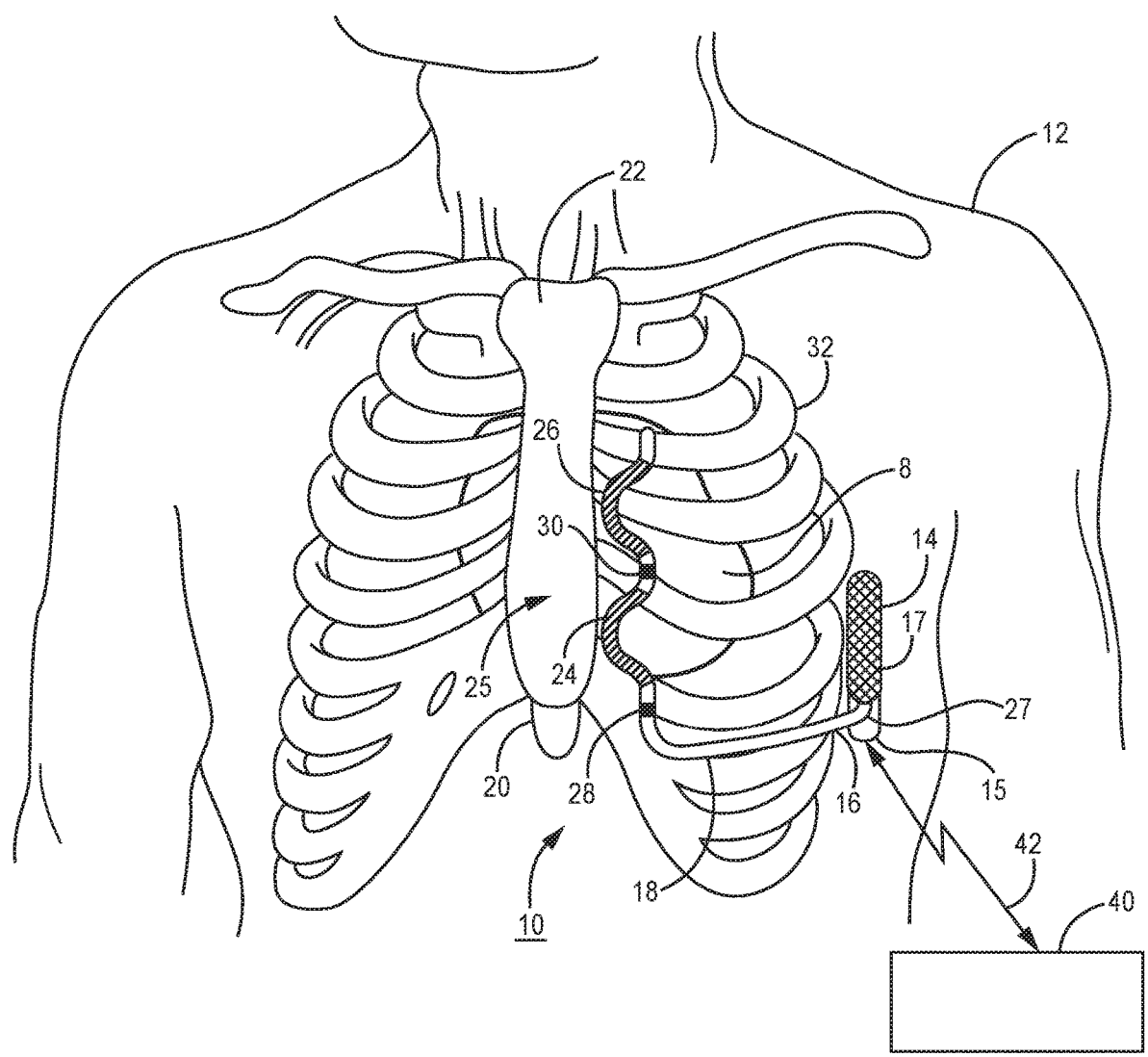
FIGS. 1A and 1B are conceptual diagrams of an extra-cardiovascular ICD system according to one example.
Figure 1B:
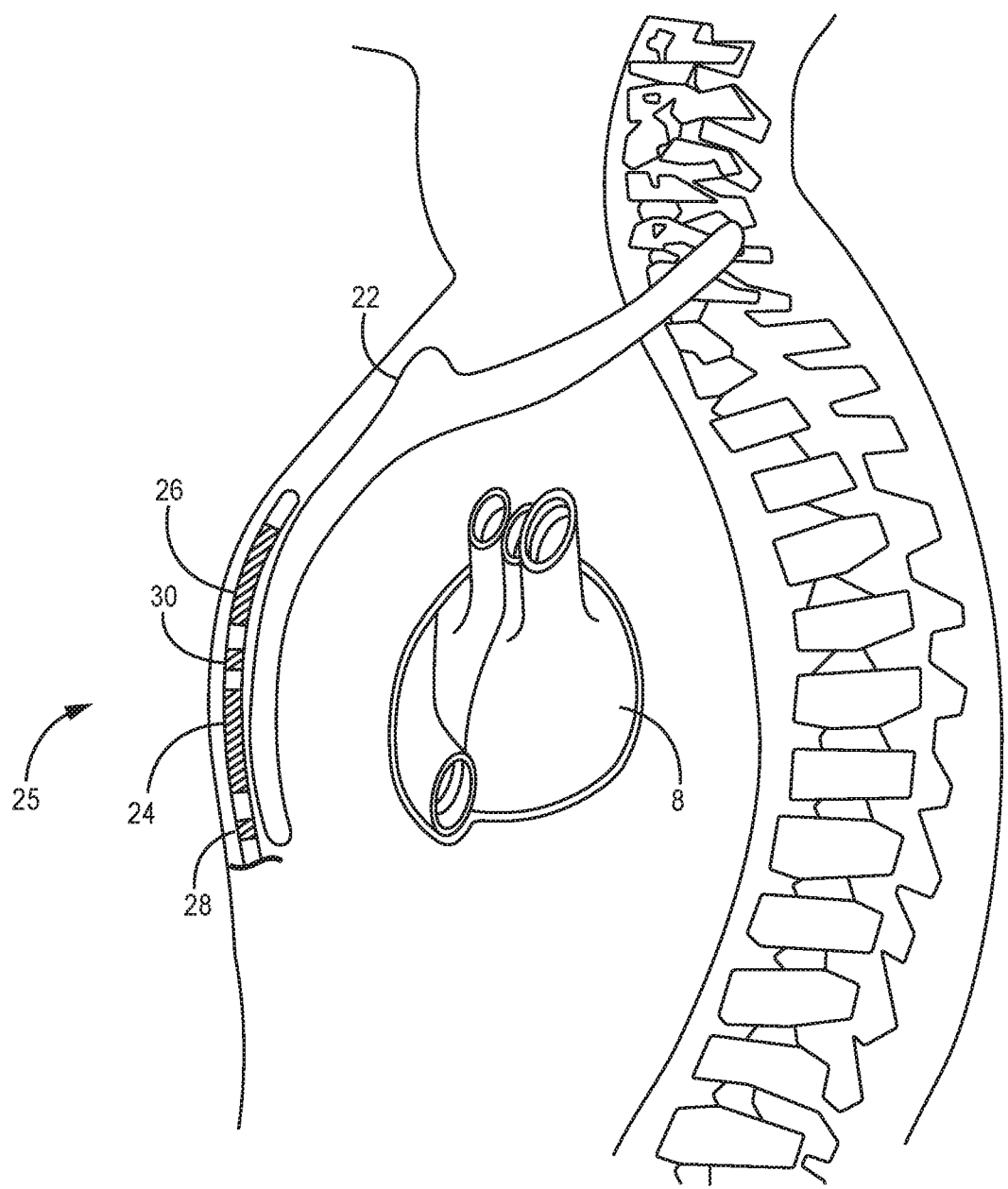

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering cardioversion/defibrillation (CV/DF) shocks or other electrical pulses including pacing pulses that may be delivered using a high voltage therapy circuit. In other examples, housing 15 may be available for use in delivering unipolar, cardiac pacing pulses from a low voltage therapy circuit and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm. Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect and discriminate abnormal rhythms such as asystole, bradycardia, non-sinus tachycardia or fibrillation and/or used in a pacing electrode vector for delivering cardiac pacing pulses to heart 8.

Electrodes 28 and 30 are relatively smaller surface area electrodes which are available for use in sensing electrode vectors for sensing cardiac electrical signals and may be used for delivering pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage cardioversion/defibrillation shocks. In some instances, electrodes 28 and 30 may provide only pacing functionality, only sensing functionality or both. ICD 14 may obtain cardiac electrical signals corresponding to electrical activity of heart 8 via one or more sensing vectors that include combinations of electrodes 24, 26, 28 and/or 30. In some examples, housing 15 of ICD 14 is used in combination with one or more of electrodes 24, 26, 28 and/or 30 in a sensing electrode vector.

In the example illustrated in FIGS. 1A and 1B, electrode 28 is located proximal to defibrillation electrode 24, and electrode 30 is located between defibrillation electrodes 24 and 26. Electrodes 28 and 30 may be positioned at other locations along lead body 18 and are not limited to the positions shown. Fewer or more pace/sense electrodes may be carried by lead 16. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a preformed curving distal portion 25 having two "C" shaped curves, which together may resemble the Greek letter epsilon, "ϵ" Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves. Various example configurations of extra-cardiovascular leads and electrodes and dimensions that may be implemented in an IMD system employing the techniques disclosed herein are described in U.S. Publication No. 2015/0306375 (Marshall, et al.) and U.S. Publication No. 2015/0306410 (Marshall, et al.), both of which are incorporated herein by reference in their entirety.

ICD 14 analyzes the cardiac electrical signals received from one or more sensing electrode vectors to monitor for abnormal rhythms, such as asystole, bradycardia, or tachyarrhythmias. ICD 14 may be configured to set pacing intervals for timing the delivery of cardiac pacing pulses according to programmed pacing therapy control parameters. ICD 14 may be configured to operate according to multiple pacing modes, e.g., VVI(R), VDI(R), VVO(R), etc., and set the pacing timing intervals accordingly. ICD 14 delivers a cardiac pacing pulse in response to a pacing timing interval expiring. For example, when a ventricular pacing interval expires without sensing an intrinsic R-wave during the pacing interval, ICD 14 delivers a pacing pulse to maintain at least a programmed minimum heart rate or provide back-up pacing during asystole, e.g., following a CV/DF shock. Cardiac pacing pulses may be delivered using defibrillation electrodes 24 and 26 as an anode and cathode pair, using pacing and sensing electrodes 28 and 30 as an anode and cathode pair, or one of pace/sense electrodes 28 or 30 paired with one of defibrillation electrodes 24 or 26, or any one of electrodes 24, 26, 28 or 30 paired with housing 15.

ICD 14 may also be configured to deliver electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may analyze the heart rate and morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated herein by reference in its entirety. ICD 14 may deliver anti-tachycardia pacing (ATP) in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15.

FIGS. 1A and 1B are illustrative in nature and should not be considered limiting of the practice of the techniques disclosed herein. ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth or protocol.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters and SVT discrimination parameters) and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
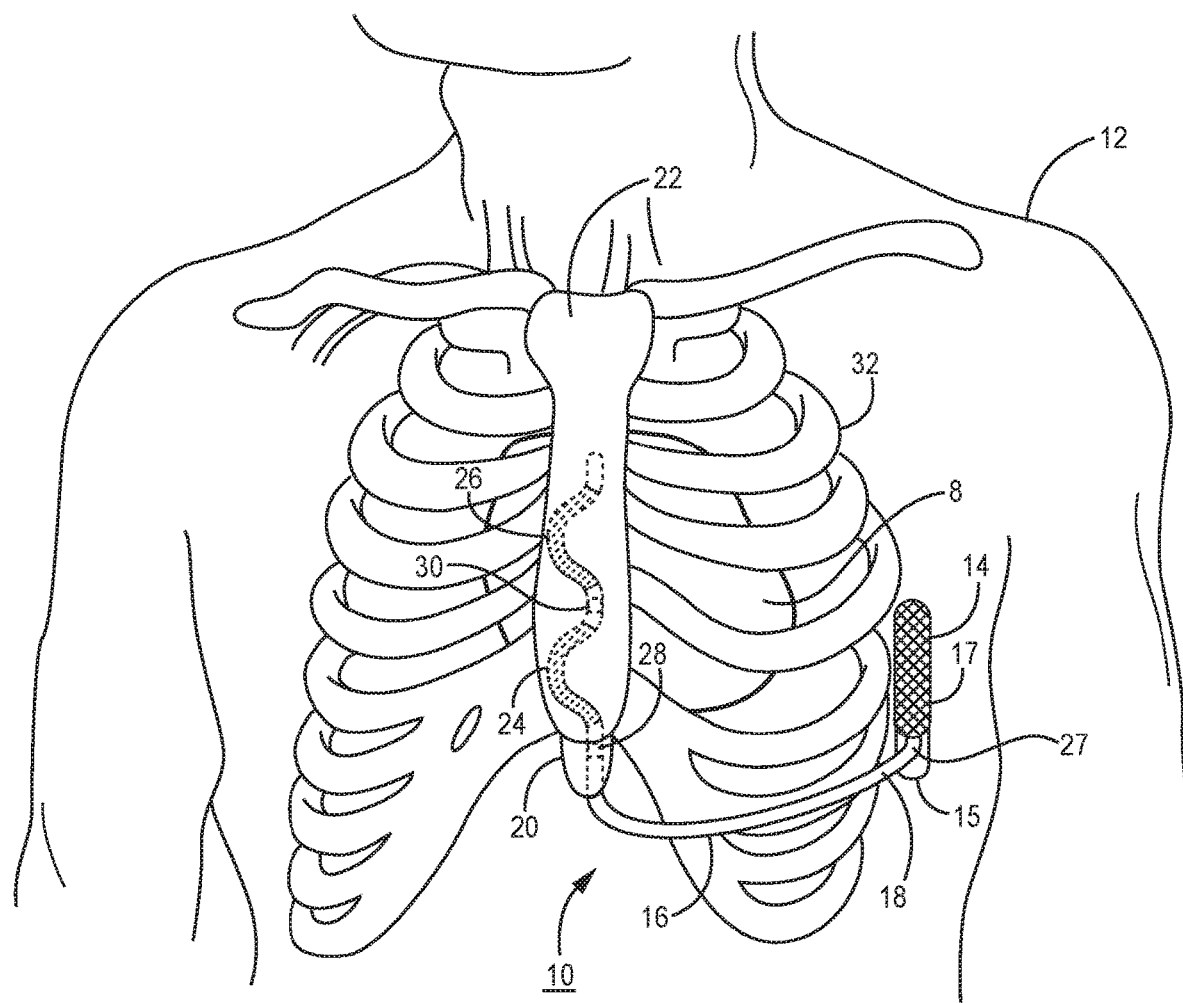
FIGS. 2A-2C are conceptual diagrams of a patient implanted with the extra-cardiovascular ICD system of FIG. 1A in a different implant configuration.
Figure 2B:
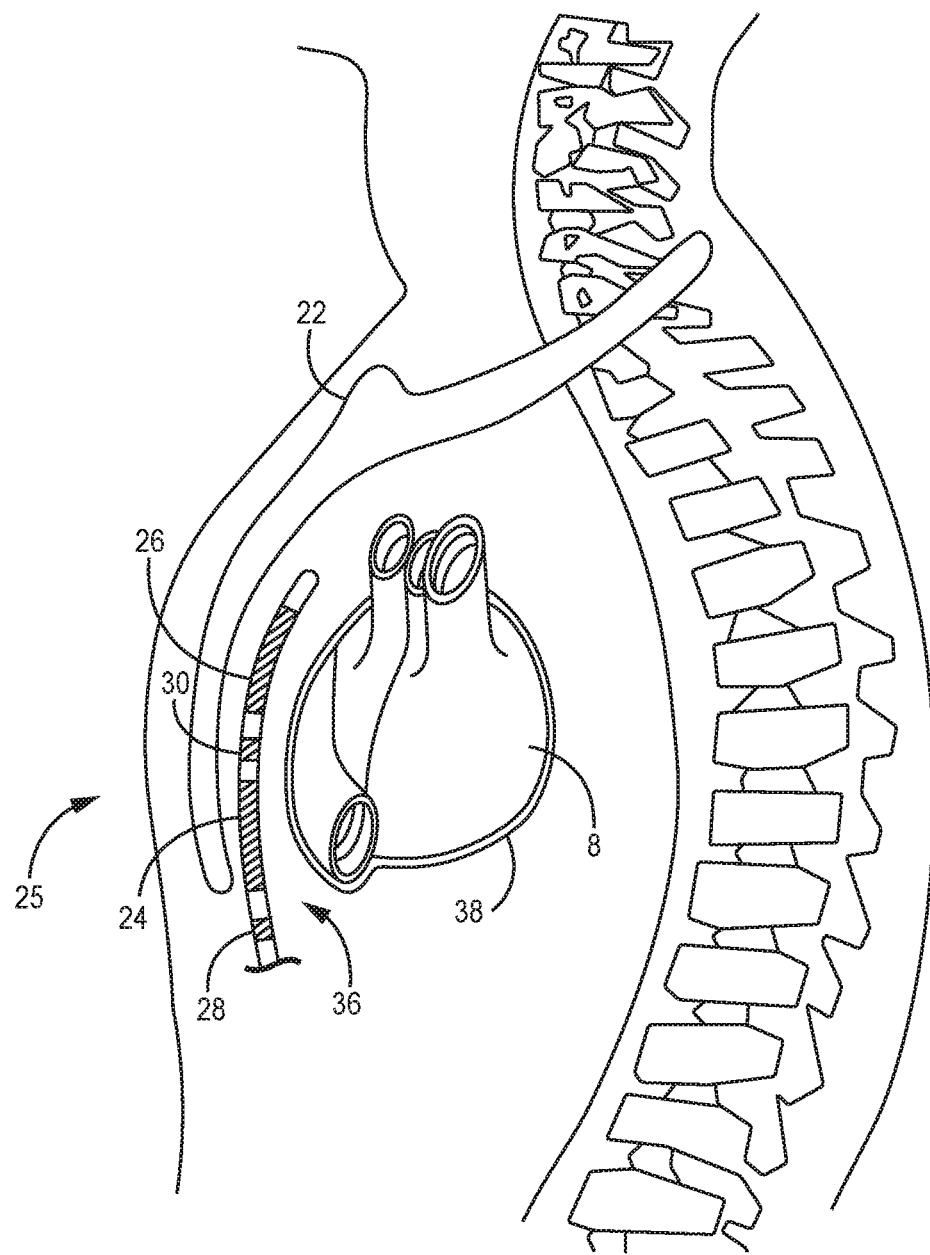
Figure 2C:
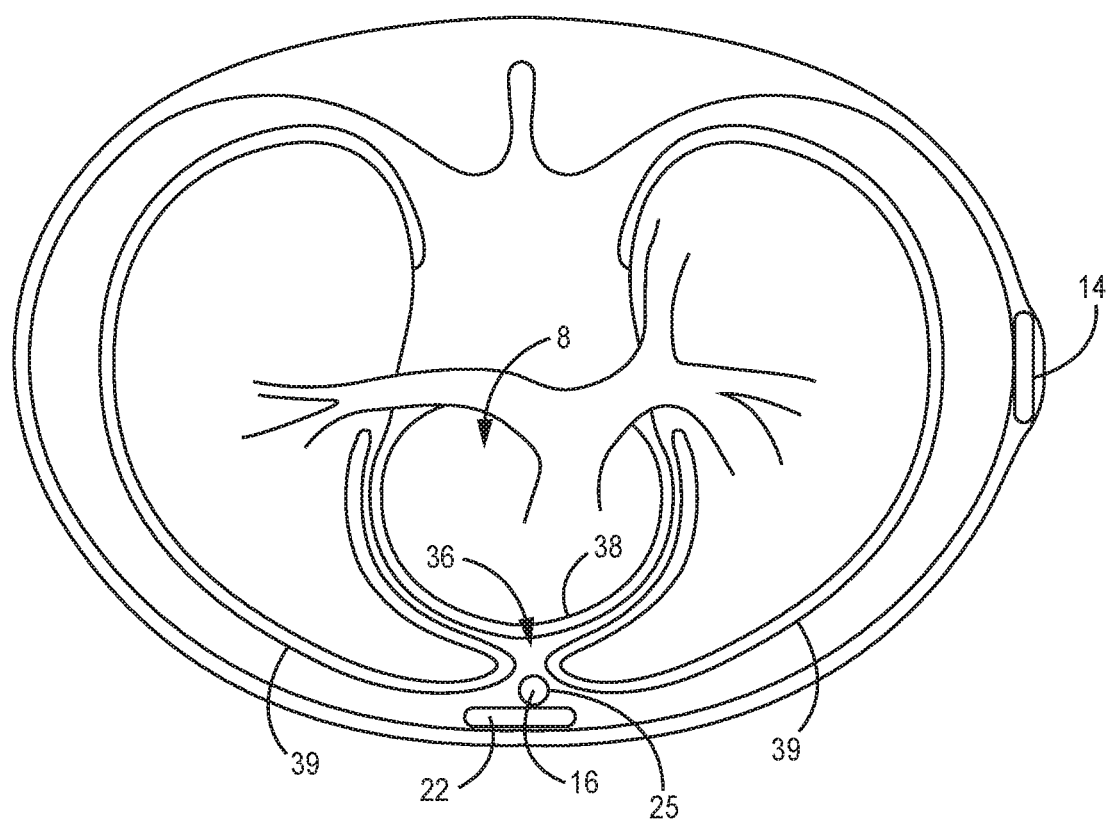

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of or within the pericardium 38 of heart 8. Other implant locations and lead and electrode arrangements that may be used in conjunction with the capacitor charging techniques described herein are generally disclosed in the above-incorporated references.

Figure 3:
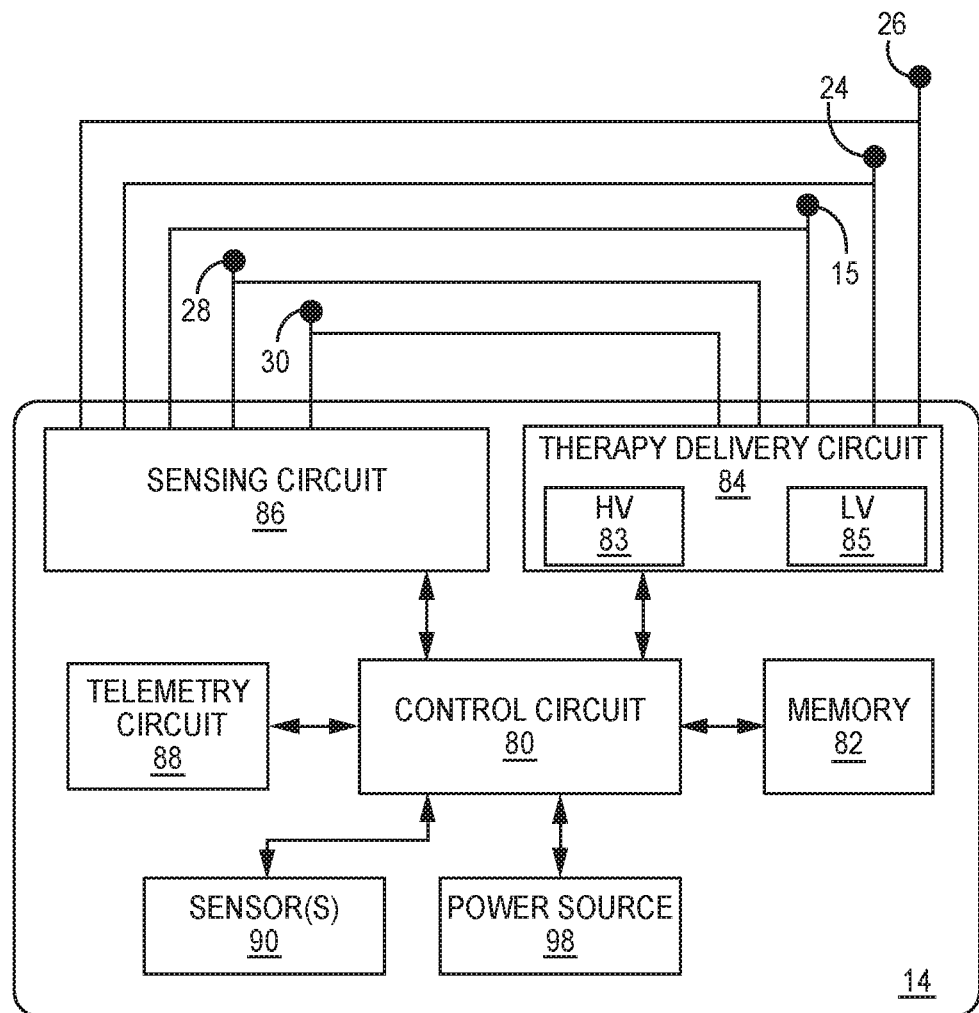
FIG. 3 is a schematic diagram of the ICD of FIGS. 1A-2C according to one example.

FIG. 3 is a schematic diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver electrical stimulation therapies as needed according to programmed therapy delivery algorithms and control parameters. ICD 14 is coupled to an extra-cardiovascular lead, such as lead 16 carrying extra-cardiovascular electrodes 24, 26, 28, and 30, for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. In some examples, ICD 14 includes one or more sensors 90 for producing a signal that is correlated to a physiological function, state or condition of the patient. A power source 98 provides power to the circuitry of ICD 14, including each of the components 80, 82, 84, 86, 88 and 90 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 is coupled to one or more charging circuits included in therapy delivery circuit 84 for providing the power needed to charge holding capacitors included in therapy delivery circuit 84 that are discharged at appropriate times under the control of control circuit 80 for producing electrical stimulation pulses according to a therapy protocol, such as for bradycardia pacing, post-shock pacing, ATP and CV/DF shock pulses. Power source 98 is also coupled to components of sensing circuit 86, such as sense amplifiers, analog-to-digital converters, switching circuitry, etc., sensors 90, telemetry circuit 88 and memory 82 to provide power to various circuits or components as needed.

The functional blocks shown in FIG. 3 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern cardiac medical device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as circuits is intended to highlight different functional aspects and does not necessarily imply that such circuits must be realized by separate hardware or software components. Rather, functionality associated with one or more circuits may be performed by separate hardware, firmware or software components, or integrated within common hardware, firmware or software components. For example, therapy control operations for delivering electrical stimulation pulses may be performed cooperatively by therapy delivery circuit 84 and control circuit 80 and may include operations implemented in a processor or other signal processing circuitry included in control circuit 80 executing instructions stored in memory 82. These therapy control operations may include controlling when holding capacitor charging to a pacing voltage amplitude is performed according to capacitor charging management techniques disclosed herein.

Control circuit 80 may include fixed function circuitry and/or programmable processing circuitry. Control circuit 80 may include any one or more of a microprocessor, a controller, a digital signal processor (DSP), an application specific integrated circuit (ASIC), a field-programmable gate array (FPGA), or equivalent discrete or analog logic circuitry. In some examples, control circuit 80 may include multiple components, such as any combination of one or more microprocessors, one or more controllers, one or more DSPs, one or more ASICs, or one or more FPGAs, as well as other discrete or integrated logic circuitry. The functions attributed to control circuit 80 herein may be embodied as software, firmware, hardware or any combination thereof.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from one or more sensing electrode vectors from the available electrodes 24, 26, 28, 30, and housing 15. Sensing circuit 86 may monitor one or more cardiac electrical signals at a time for sensing cardiac electrical events, e.g., P-waves attendant to the depolarization of the atrial myocardium and/or R-waves attendant to the depolarization of the ventricular myocardium, and providing digitized cardiac signal waveforms for analysis by control circuit 80. For example, sensing circuit 86 may include switching circuitry for selecting which of electrodes 24, 26, 28, 30, and housing 15 are coupled to cardiac event detection circuitry. Switching circuitry may include a switch array, switch matrix, multiplexer, or any other type of switching device suitable to selectively couple components of sensing circuit 86 to selected electrodes.

The cardiac event detection circuitry may be configured to amplify, filter and digitize the cardiac electrical signal received from selected electrodes to improve the signal quality for detecting cardiac electrical events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac electrical event based on a sensing threshold crossing, sensing circuit 86 may produce a sensed event signal, such as an R-wave sensed event signal, that is passed to control circuit 80. The R-wave sensed event signal is used by control circuit 80 for restarting a pacing escape interval timer that controls the basic time intervals used for scheduling cardiac pacing pulses. For example, in a VVI pacing mode, a ventricular pacing interval (or VV interval) may be restarted in response to each R-wave sensed event signal that is received outside a blanking period to inhibit a scheduled pacing pulse. The ventricular pacing interval is started in response to each delivered pacing pulse to control the minimum heart rate and timing of pacing pulses delivered by therapy delivery circuit 84.

Control circuit 80 may also use the R-wave sensed event signals corresponding to intrinsic (non-paced) heart depolarizations to determine RR intervals (RRIs) for detecting tachyarrhythmia and determining a need for therapy. An RRI is the time interval between two consecutively sensed intrinsic R-waves and may be determined between two consecutive R-wave sensed event signals received from sensing circuit 86. Control circuit 80 may be configured to detect a tachyarrhythmia based on RRIs and/or the morphology of QRS waveforms received as multi-bit digitized signals from sensing circuit 86. Therapy delivery circuit 84 is controlled to deliver ATP and/or CV/DF shock pulses according to programmed therapy protocols in response to detecting ventricular tachycardia or fibrillation.

In this example, therapy delivery circuit 84 includes a high voltage (HV) therapy circuit 83 and may include a low voltage (LV) therapy circuit 85. Each therapy circuit 83 and 85 includes charging circuitry, one or more charge storage devices such as one or more high voltage holding capacitors or low voltage holding capacitors, respectively, and switching circuitry that controls when the capacitor(s) are charged and discharged across a selected CV/DF shock vector or pacing electrode vector. Charging of capacitors to a programmed pacing voltage amplitude and discharging of the capacitors for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

Therapy delivery circuit 84 is controlled by control circuit 80 to charge one or more holding capacitors according to a capacitor charging mode. As described herein, the therapy delivery circuit 84 may be configured to charge one or more holding capacitors according to a delayed charging mode in which capacitor charging is withheld for at least a portion of or all of a pacing interval. The holding capacitor voltage may be allowed to fall below the pacing voltage amplitude during a pacing interval without being recharged. At other times, therapy delivery circuit 84 may be controlled to charge one or more holding capacitors according to a charging without delay mode, during which capacitor charging is not withheld and may be performed from the beginning or throughout a pacing interval as needed to maintain the holding capacitor charge at the pacing voltage amplitude. Control circuit 80 may be configured to control therapy delivery circuit to switch between the delayed capacitor charging mode and the capacitor charging without delay mode based on intrinsic heart rate criteria determined from the cardiac electrical signal(s) received by sensing circuit 86 and/or other signals received from sensor(s) 90.

Components that may be included in HV therapy circuit 83 and LV therapy circuit 85 are described below in conjunction with FIGS. 4 and 5, respectively. It is recognized that the methods disclosed herein for controlling capacitor charging for pacing therapy may be implemented in an IMD system that includes only a HV therapy circuit 83 configured to deliver cardiac pacing pulses, which may be in addition to high voltage CV/DF shock delivery capabilities, or in an IMD system that includes only LV therapy circuit 85 without CV/DF shock therapy capabilities. In some systems, HV therapy circuit 83 delivers only high voltage CV/DF shock pulses, and LV therapy circuit 85 delivers relatively lower voltage pacing pulses. In other examples, control circuit 80 may selectively control which one of HV therapy circuit 83 or LV therapy circuit 85 is utilized for generating and delivering cardiac pacing pulses based on the type of pacing therapy, the pacing threshold voltage amplitude required to capture the heart, or other factors.

ICD 14 may include other sensors 90 for sensing signals from the patient for use in determining a need for and/or controlling electrical stimulation therapies delivered by therapy delivery circuit 84. In some examples, a sensor indicative of a need for increased cardiac output may be included in ICD 14, such as a tissue oxygen sensor, an impedance sensor, or a pressure sensor. A sensor indicative of a need for increased cardiac output may include a patient activity sensor, such as an accelerometer, or an impedance sensor for determining minute volume or other respiratory metrics. An increase in the metabolic demand of the patient due to increased activity may be determined by control circuit 80 from a sensor signal received from sensors 90 for use in determining a need for pacing or a need for an increased pacing rate. Likewise, a sensor signal may be used by control circuit 80 for determining when a need for pacing no longer exists or when the pacing rate may be decreased.

Control circuit 80 may be configured to use a sensor signal from sensors 90 to detect a need for pacing and/or an expected increased pacing burden. "Pacing burden" as used herein may be defined as the percentage of time the patient's heart rhythm is a paced rhythm (as opposed to an intrinsic rhythm) over a predetermined period of time. For example, the patient may be paced 10% of the time over a 24-hour period. In other examples, pacing burden may be determined as the proportion of paced events to sensed intrinsic events or the proportion of paced events to all paced and sensed intrinsic events combined over a predetermined time period or total number of cardiac events. Control circuit 80 may be configured to detect an expected increase in pacing burden based on a physiological condition of the patient, such as reduced cardiac output, increased patient activity, low tissue oxygenation, or other condition for which an increased pacing frequency and/or rate is expected to improve or alleviate.

The control circuit 80 may respond to detecting an expected change in pacing burden by enabling switching between different capacitor charging modes. For example, control circuit 80 may respond to an increase in expected pacing burden by enabling therapy delivery circuit 84 to switch between capacitor charging without delay and delayed capacitor charging based on whether increased intrinsic heart rate criteria and/or decreased intrinsic heart rate criteria are met. Enabling (turning on) the function of switching between capacitor charging modes does not necessarily require immediately making the switch from one charging mode to another. Rather, after criteria required to be satisfied for enabling the function of switching between capacitor charging modes, additional criteria relating to the intrinsic heart rate and/or sensor signals may be required to be met before actually performing the switch from one capacitor charging mode to another.

In other examples, control circuit 80 may respond to detecting a change in expected pacing burden based on a signal from sensors 90 by directly switching the capacitor charging mode. For example, when the pacing burden is expected to be decreased, e.g., due to a restored cardiac output, tissue oxygenation, blood pressure, or reduced patient activity, the control circuit 80 may control the therapy delivery circuit 84 to switch the capacitor charging pacing mode to delayed capacitor charging to conserve energy of power source 98. Methods for enabling the function of automatic switching between capacitor charging modes and methods for controlling the timing of the switching between capacitor charging modes after the switching function is enabled are described in greater detail below in conjunction with the flow charts and timing diagrams presented herein.

Control parameters utilized by control circuit 80 for sensing cardiac events, detecting cardiac arrhythmias and controlling therapy delivery, including controlling capacitor charging techniques as disclosed herein, may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 4:
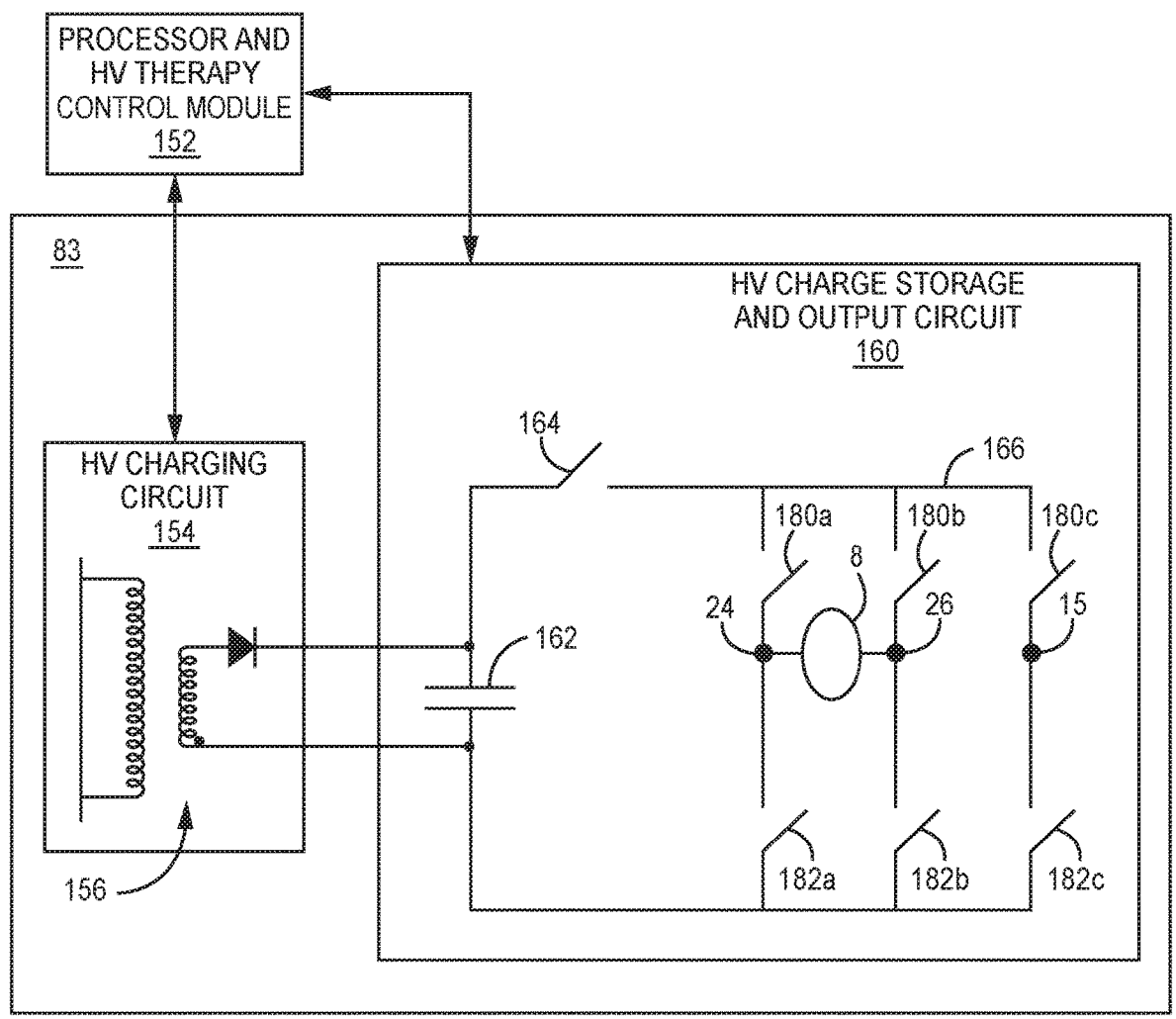
FIG. 4 is diagram of a high voltage therapy circuit of the ICD of FIG. 3 according to one example.

FIG. 4 is schematic diagram 150 of HV therapy circuit 83 included in ICD 14 according to one example. HV therapy circuit 83 includes a HV charging circuit 154 and a HV charge storage and output circuit 160. HV therapy circuit 83 is shown coupled to a processor and HV therapy control circuit 152 which may be included in control circuit 80 for controlling HV charging circuit 154 and HV charge storage and output circuit 160. HV charge storage and output circuit 160 includes a HV holding capacitor 162 coupled to switching circuitry 166 via a pulse control switch 164 for coupling the HV holding capacitor 162 to electrodes 24, 26 and/or housing 15 to deliver a desired electrical stimulation pulse, which may be a pacing pulse or a CV/DF shock pulse, to the patient's heart 8. In other examples, pacing and sensing electrodes 28 and 30 (not shown in FIG. 4) may be selectively coupled to HV holding capacitor 162 via switching circuitry 166 for using one or both of electrodes 28 and 30 in a pacing electrode vector for delivering a pacing pulse from HV therapy module 83.

HV holding capacitor 162 is shown schematically as a single capacitor, but it is recognized that a bank of two or more capacitors or other energy storage devices may be used to store energy for producing electrical signals delivered to heart 8. In one example, HV capacitor 162 is a series of three capacitors having an effective capacitance of 148 microfarads. HV holding capacitor 162 is charged to a desired pacing pulse voltage amplitude (or shock voltage amplitude in the case of a CV/DF shock delivery) by HV charging circuit 154 under the control of processor and HV therapy control 152. It is to be understood that charging to a pacing voltage amplitude may include charging to a specified tolerance within or greater than the pacing voltage amplitude. For example, charging to the pacing voltage amplitude may include charging to 113% (or another predetermined percentage) of the programmed pacing voltage amplitude.

HV charging circuit 154 receives a voltage regulated signal from power source 98 (FIG. 3). HV charging circuit 154 includes a transformer 156 to step up the battery voltage of power source 98 in order to achieve charging of HV holding capacitor 162 to a voltage that is much greater than the battery voltage. Charging of capacitor 162 by HV charging circuit 154 is performed under the control of processor and HV therapy control 152, which receives feedback signals from HV charge storage and output circuit 160 to determine when capacitor 162 is charged to a programmed voltage. A charge completion signal is passed to HV charging circuit 154 to terminate charging by processor and HV therapy control module 152. One example of a high voltage charging circuit and its operation is generally disclosed in U.S. Pat. No. 8,195,291 (Norton, et al.), incorporated herein by reference in its entirety.

When the capacitor charging is being controlled in a capacitor charging without delay mode, charging of HV holding capacitor 162 may occur continuously or semi-continuously throughout a pacing interval started in response to a delivered pacing pulse or sensed intrinsic event. Continuous charging during a pacing interval may be achieved by comparing the feedback signal from HV charge storage and output circuit 160 to the targeted pacing voltage amplitude (plus or minus any tolerance) and performing top-off charging of capacitor 162 as needed to maintain the capacitor at a desired voltage. For example, the capacitor charge feedback signal may be compared to the targeted pacing voltage amplitude on every interrupt signal from control circuit 80 or other predetermined frequency during a pacing interval. Whenever the charge is below the pacing voltage amplitude, the capacitor 162 is charged as needed to maintain the charge at the programmed pacing voltage amplitude throughout the pacing interval.

In other examples of a charging without delay mode, the charge of capacitor 162 may be compared to the targeted pacing voltage amplitude at the start of a pacing interval and charged up to the pacing voltage amplitude (plus any specified tolerance) one time during the pacing interval, without monitoring/charging throughout the pacing interval. If a pacing pulse is delivered or leakage of the capacitor charge occurs during the pacing interval after charging, the capacitor charge is topped off at the beginning of the next pacing interval.

As described in conjunction with the timing diagrams and flow charts presented herein, the processor and HV therapy control 152 may be configured to withhold charging of HV holding capacitor 162 when increased heart rate criteria and/or decreased pacing burden criteria are satisfied. The capacitor charging may be delayed or withheld by processor and HV therapy control 152 until a pacing interval expires or until a capacitor charging delay interval expires.

When HV holding capacitor 162 is charged to a desired pacing voltage amplitude and a pacing interval expires, the HV holding capacitor 162 is coupled across the desired pacing electrode vector via pulse control switch 164 and switching circuitry 166 to deliver the pacing pulse. Switching circuitry 166 may be in the form of an H-bridge and may include switches 180a-180c and 182a-182c that are controlled by signals from processor and HV control circuit 152. Switches 180a-180c and 182a-182c may be implemented as silicon-controlled rectifiers (SCRs), insulated-gate bipolar transistors (IGBTs), metal-oxide-semiconductor field-effect transistors (MOSFETs), and/or other switching circuit components. Switches 180a-180c and 182a-182c are controlled to be open or closed by processor and HV therapy control circuit 152 at the appropriate times for delivering a monophasic, biphasic or other desired pacing pulse by discharging capacitor 162 across the pacing load presented by heart 8 and a selected pacing electrode vector. The HV holding capacitor 162 is coupled across the selected pacing electrode vector for the programmed pacing pulse width via pulse control switch 164.

For instance, the selected electrodes 24, 26 and/or housing 15 may be coupled to HV holding capacitor 162 by opening (i.e., turning off or disabling) and closing (i.e., turning on or enabling) the appropriate switches of switching circuitry 166 to pass a desired electrical signal to the therapy delivery electrode vector. The electrical signal may be a monophasic, biphasic or other shaped signal. The signal may be a monophasic or biphasic pacing pulse delivered in response to a pacing interval expiring such as a VVI pacing interval, a post-shock pacing interval or an ATP interval. At other times, the signal may be a CV/DF shock for terminating a ventricular tachyarrhythmia when VT or VF is detected.

To deliver a pacing pulse, for example, one of switches 180a, 180b or 180c may be closed simultaneously with one of switches 182a, 182b, or 182c without closing both of the "a," "b" or "c" switches across a given electrode 24, 26 or housing 15, respectively, at the same time. To deliver a biphasic pulse using electrode 24 and housing 15, for instance, switch 180a and 182c may be closed to deliver a first phase of the biphasic pulse. Switches 180a and 182c are opened after the first phase, and switches 180c and 182a are closed to deliver the second phase of the biphasic pulse. Switches 180b and 182b remain open or disabled in this example with electrode 26 not selected or used in the therapy delivery vector. In other examples, electrode 26 may be included instead of electrode 24 or simultaneously activated with electrode 24.

After delivering a pacing pulse, the HV holding capacitor 162 may be re-charged to the programmed pacing pulse amplitude if increased intrinsic heart rate detection criteria are not satisfied. Processor and HV therapy control 152, however, may withhold charging of HV holding capacitor 162 to the pacing voltage amplitude in response to determining that increased intrinsic heart rate criteria are satisfied using the techniques disclosed herein. When the rate of intrinsic events sensed by sensing circuit 86 of ICD 14, the slope of the rate of intrinsic events, and/or other criteria satisfy increased intrinsic heart rate detection criteria and/or decreased pacing burden criteria, charging of HV holding capacitor 162 may be withheld until a pacing interval expires or until a predetermined charging delay interval expires. Processor and HV therapy control circuit 152 may revert to charging HV holding capacitor 162 without delay, e.g., at the beginning of a pacing interval or throughout a pacing interval started in response to a pacing pulse or a sensed event signal as needed, in response to determining that decreased intrinsic heart rate criteria and/or decreased pacing burden criteria are met as described below.

Figure 5:
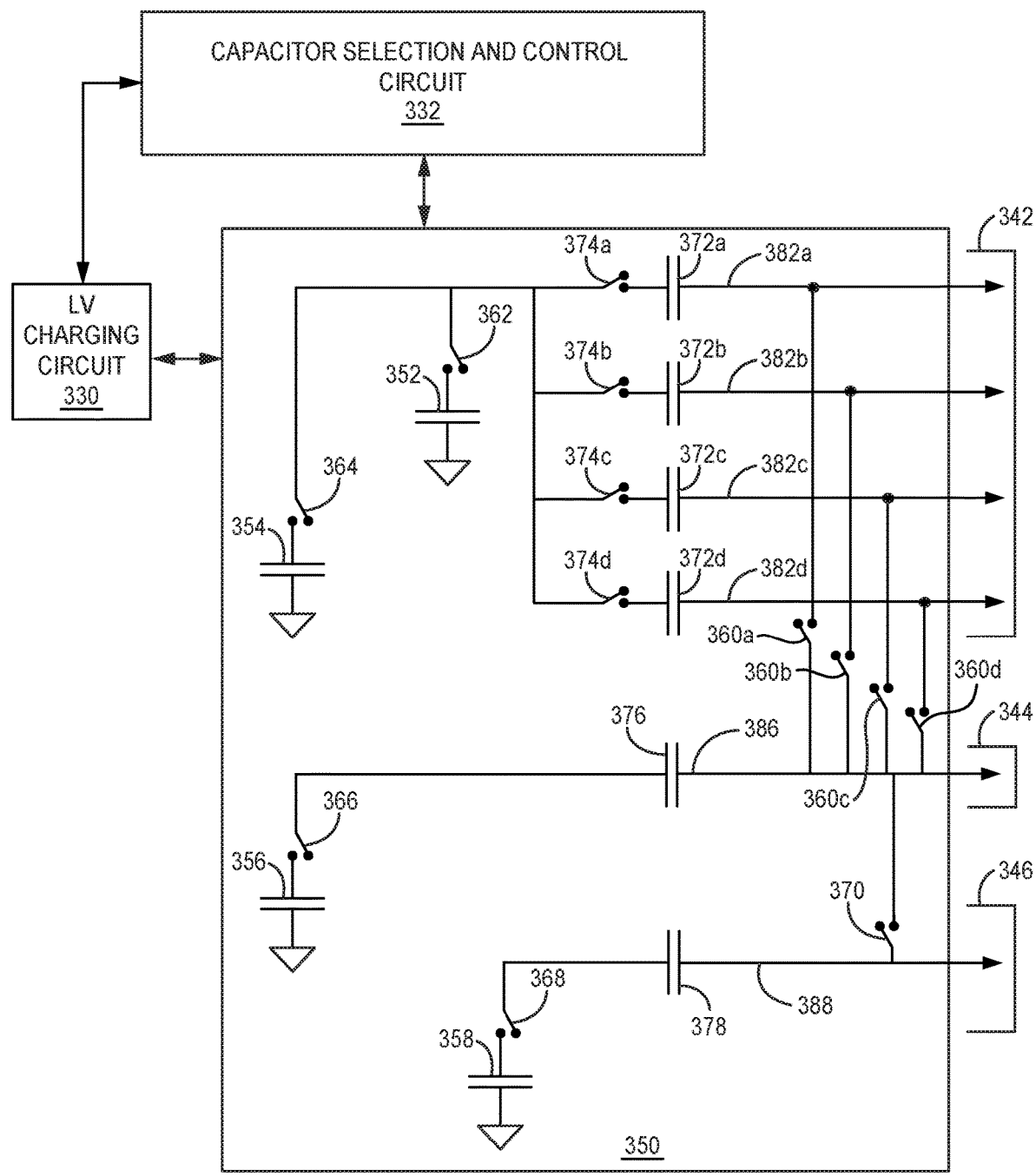
FIG. 5 is a diagram of a low voltage therapy circuit of the ICD of FIG. 3 according to one example.

FIG. 5 is a conceptual diagram of LV therapy circuit 85 according to one example. LV therapy circuit 85 may include a LV charging circuit 330, a capacitor selection and control circuit 332, and a capacitor array 350. Capacitor array 350 may include multiple LV holding capacitors 352, 354, 356 and 358 that can each be charged by LV charging circuit 350 to a programmed pacing voltage amplitude. The LV holding capacitors 352, 354, 356 and 358 are coupled to a respective output capacitor 372a-372d (collectively 372), 376, or 378 via respective switches 362, 364, 366, and 368 to deliver pacing pulses. Each of LV holding capacitors 352, 354, 356 and 358 may have a capacitance that is less than the effective capacitance of HV holding capacitor 162 of HV therapy circuit 83. For example, each of holding capacitors 352, 354, 356 and 358 may have a capacitance of up to 6 microfarads, up to 10 microfarads, up to 20 microfarads or other selected capacitance, but all may have a capacitance significantly less than the effective capacitance of HV holding capacitor 162 and have a lower voltage rating than HV holding capacitor 162.

Power source 98 (FIG. 3) may provide regulated power to LV charging circuit 330. LV charging circuit 330 may be controlled by a state machine in capacitor selection and control circuit 332 to charge all or selected LV holding capacitors 352, 354, 356 and 358 using a multiple of the battery voltage of power source 98, e.g., four times the battery voltage. LV charging circuit 330 charges one or more of capacitors 352, 354, 356 and 358 as needed for delivering a pacing pulse to the patient's heart via a selected pacing electrode vector. The pacing pulse may be a single pacing pulse delivered by discharging a single LV holding capacitor for a programmed pulse width. In other examples, two or more of LV holding capacitors 352, 354, 356 and 358 may be discharged sequentially to deliver two or more fused pulses within a pacing pulse width to deliver a composite pacing pulse.

In some examples, the LV therapy circuit 85 includes three pacing channels 342, 344 and 346. Each pacing channel is capable of producing a single pacing pulse when a respective LV holding capacitor 352, 356 or 358 is discharged across an output capacitor 372, 376, or 378, respectively. Pacing channel 342 includes a back-up holding capacitor 354 that may be used for delivering back-up pacing pulses. Back-up holding capacitor 354 may be used to deliver an individual pulse of a composite pacing pulse. Depending on the number of extra-cardiovascular electrodes coupled to ICD 14, one or more channels may include multiple selectable output signal lines. For example, channel 342 is shown in this example to include multiple selectable pacing output signal lines 382a-382d that may be selectively coupled to LV holding capacitor 352 and back-up holding capacitor 354 via closure of one or more of electrode selection switches 374a-374d. For example, multiple electrodes carried by lead 16 may be coupled to pacing channel 342, and a pacing electrode vector may be selected from the multiple electrodes by closing certain ones of switches 374a-374d.

Pacing channels 344 and 346 are shown having single output signal lines 386 and 388 that are coupled to respective LV holding capacitors 366 and 368 via respective switches 366 and 368. In other examples, all three pacing channels 342, 344 and 346 may be provided with a single output signal line or with multiple output signal lines to enable selection of a pacing electrode vector from among multiple extra-cardiovascular electrodes coupled to ICD 14, e.g., any of electrodes 24, 26, 28, or 30 of lead 16 shown in FIG. 1A.

When a pacing therapy is needed, control circuit 80 may control LV therapy circuit 85 to select any one or combination of the pacing channels 342, 344 and 346 to deliver a pacing pulse. The pacing pulse may be a single-pulse pacing pulse delivered by discharging one of the holding capacitors 352, 354, 356 or 358 across a selected pacing electrode vector via a respective output capacitor 374, 376 or 378 when a respective switch 362, 364, 366 or 368 is closed. The output line 382a, 382b, 382c, or 382d used to deliver pacing current from pacing channel 342 may be selected via a respective electrode selection switch 372a-372d. The switch 362, 364, 366 or 368 that enables discharge of a holding capacitor 352, 354, 356 or 358, respectively, may be enabled by capacitor selection and control circuit 332 at the appropriate time when a pacing pulse is needed and maintained in an active, enabled (closed) state until the single-pulse pacing pulse width is expired.

In some patients, a single-pulse pacing pulse generated by LV therapy circuit 85 may not have the pulse energy required to capture the patient's heart. Control circuit 80 may control LV therapy circuit 85 to deliver fused pulses in a multi-pulse composite, pacing pulse. Two or all three pacing channels 342, 344 and 346 are tied together by switches 360a-d and 370 to enable individual pulses to be delivered across a selected pacing electrode vector from a single output signal line 344. For example, control circuit 80 may control LV therapy circuit 85 to deliver a multi-pulse, composite pacing pulse by activating at least one of switches 360a-d and switch 370 to tie at least one of pacing output lines 382a-d and pacing output line 388 to pacing channel 344. Control circuit 80 controls capacitor selection and control circuit 332 to enable pacing channel switches 362, 364, 366 and 368 (and at least one electrode selection switch 372a-d of pacing channel 342) in a sequential manner to sequentially couple two or more of the respective holding capacitors 352, 354, 356 or 358 to output signal line 386 to deliver a sequence of at least two fused, individual pulses to produce a composite pacing pulse.

In various examples, depending on the particular pacing channel and lead and electrode configuration used with ICD 14, some electrode selection switches shown in FIG. 5 may not be required. Furthermore, it is recognized that less than four holding capacitors or more than four holding capacitors may be included in a capacitor array 350 for use in delivering a sequence of fused pulses in a composite pacing pulse when the LV therapy circuit 85 is controlled to deliver a pacing pulse.

Capacitor selection and control circuit 332 selects which holding capacitors 352, 354, 356 or 358 are coupled to output line 386 and in what sequence by controlling respective switches 362, 364, 366 and 368. A sequence of pulses may be delivered to produce a composite pacing pulse by sequentially discharging holding capacitors 352, 354, 356 or 358 one at a time (or one combination at a time) across a respective output capacitor 372, 376 or 378 by sequentially enabling or closing the respective switches 362, 364, 366 or 368. For example, at least two of holding capacitors 352, 354, 356 or 358 are sequentially discharged to produce a composite pacing pulse produced by at least two fused individual pulses. Output line 386 may be electrically coupled to a pacing cathode electrode carried by lead 16 and a return anode electrode carried by lead 16 (or housing 15) may be coupled to ground. The pacing cathode electrode and return anode electrode may correspond to electrodes 28 and 24, respectively, as shown in FIG. 1A in one example, however any pacing electrode vector may be selected from electrodes 24, 26, 28, and 30 and/or housing 15 shown in FIG. 1A.

In some examples, a low-voltage, fused pacing pulse is delivered by delivering an individual pulse from pacing channel 344 and 346 sequentially followed by a third, longer individual pulse delivered by pacing channel 342 by discharging both capacitors 352 and 354 simultaneously. The first two individual pulses may be 2.0 ms in pulse width and the third pulse may be 4.0 ms in pulse width for a composite pacing pulse width of 8 ms. The higher capacitance of the parallel capacitors 312 and 314 allows for the third individual pulse to be longer in pulse width while maintaining a pulse amplitude that successfully captures the heart. All three individual pulses are delivered via output line 386 by controlling output configuration switches 360 and 370 to couple the capacitors 352, 354 and 358 to output line 386. Other examples of a LV therapy circuit and pacing pulse generation techniques that may be used in conjunction with the techniques disclosed herein are generally disclosed in U.S. patent application Ser. No. 62/262,412 and the corresponding U.S. patent application Ser. No. 15/368,197.

The LV holding capacitors 352, 354, 356 and/or 358 selected for use in generating a single-pulse pacing pulse or a multi-pulse, composite pacing pulse may be charged by LV charging circuit 330 according to the capacitor charging control techniques disclosed herein. When criteria for detecting an increased intrinsic heart rate are satisfied, charging of LV holding capacitors 352, 354, 356 and/or 358 used for generating pacing pulses may be withheld or delayed according to a delayed capacitor charging pacing mode. Charging is delayed until a pacing interval expires in some examples or until a capacitor charging delay interval expires in other examples. If criteria for detecting a decreased intrinsic heart rate are satisfied, charging of the LV holding capacitors 352, 354, 356 or 358 used for generating and delivering pacing pulses is performed without delay, e.g., at the beginning of a pacing interval or throughout the pacing interval as generally described above in conjunction with FIG. 4.

Control circuit 80 may enable the function of automatic switching between capacitor charging modes based on pacing burden criteria in some examples, as described in further detail herein. After automatic switching between charging modes is enabled based on a change in the actual or expected pacing burden, control circuit 80 may switch between controlling LV charging circuit 330 according to a delayed charging mode and a charging without delay mode. The switching between the charging modes may be controlled based on intrinsic heart rate criteria and/or pacing burden criteria.

Figure 6:
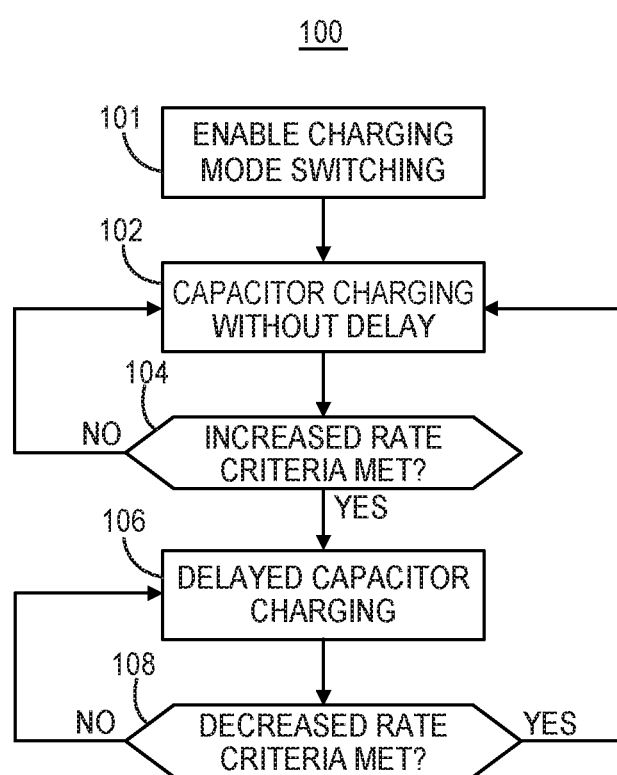
FIG. 6 is a flow chart of a method for controlling capacitor charging for pacing pulse delivery according to one example.

FIG. 6 is a flow chart 100 of one method for controlling holding capacitor charging for pacing pulse delivery. At block 101, control circuit 80 enables automatic switching between a first capacitor charging mode and a second capacitor charging mode. In some examples, charging mode switching is enabled in response to a user command received from external device 40 via telemetry circuit 88. In other examples, control circuit 80 may automatically enable and/or disable charging mode switching based on determining an actual or expected change in pacing burden, e.g., as described in conjunction with FIG. 12 below. The two charging modes may include a delayed charging mode and a charging without delay mode.

In the example shown in FIG. 6, ICD 14 may initially be operating in a capacitor charging without delay mode. In this charging mode, one or more holding capacitors are charged to the pacing voltage amplitude during each pacing interval according to a selected pacing output configuration, e.g., using either HV therapy circuit 83 or LV therapy circuit 85 as described above. The pacing interval is set by control circuit 80 in response to a delivered pacing pulse or sensed cardiac event, e.g., an intrinsic R-wave, to control the timing of pacing pulses, e.g., according to a VVI or other pacing mode. The holding capacitor charging is performed without delay such that charging may begin at the start of the pacing interval and/or occur at any time during the pacing interval in response to a comparison of the holding capacitor charge to the programmed pacing voltage. If the holding capacitor charge is less than the programmed pacing voltage amplitude (or less than a tolerance below the pacing voltage amplitude), control circuit 80 controls therapy delivery circuit 84 to charge the holding capacitor to the programmed pacing voltage amplitude.

While operating in the capacitor charging without delay mode, control circuit 80 monitors the cardiac electrical signal received by sensing circuit 86 for determining if increased intrinsic heart rate criteria are met at block 104. Increased intrinsic heart rate criteria may require that the intrinsic heart rate be equal to or greater than a predetermined mode switching heart rate threshold. The mode switching heart rate threshold may be defined to be faster than the current pacing rate such that mode switching does not necessarily occur in response to one or more sensed events occurring at event intervals shorter than the pacing interval and resulting in one or more inhibited pacing pulses. For instance, charging mode switching may not occur if the heart rate is between the pacing rate and the mode switching heart rate threshold. Various techniques for determining if increased intrinsic heart rate criteria are met are described below, e.g., in conjunction with FIGS. 7 and 12.

If the increased intrinsic rate criteria are satisfied at block 104, control circuit 80 switches to the second charging mode, the delayed capacitor charging mode in this example, at block 106. In this mode, control circuit 80 may withhold comparisons between the holding capacitor charge and the programmed pacing voltage amplitude and/or withhold charging of the holding capacitor(s) even when the capacitor charge is less than the pacing voltage amplitude. Capacitor charging is withheld for at least a portion of the pacing interval started in response to a cardiac event, either a delivered pacing pulse or a sensed intrinsic event. Charging may be withheld for the entire pacing interval in some examples. In other examples, charging is withheld until expiration of a charging delay interval. If an intrinsic event is sensed prior to expiration of the charging delay interval, no charging occurs and the pacing interval is restarted.

During the delayed capacitor charging mode, control circuit 80 monitors the cardiac electrical signal for determining whether decreased intrinsic heart rate criteria are met at block 108. The decreased intrinsic heart rate criteria may be satisfied in response to one or more pacing intervals expiring and/or one or more charging delay intervals expiring. As such, in some examples decreased intrinsic heart rate criteria may be satisfied in response to a decreasing intrinsic heart rate before the intrinsic heart rate falls below the pacing rate, before a pacing interval expires. In response to the decreased intrinsic heart rate criteria being met, control circuit 80 switches back to the capacitor charging without delay mode at block 102. Methods for determining if decreased intrinsic heart rate criteria are described in greater detail below, e.g., in conjunction with FIGS. 7, 8A-D, and 12.

In this way, capacitor charging is controlled according to a delayed capacitor charging mode after increased intrinsic heart rate criteria are met and the potential need for a pacing pulse is expected to be low. Capacitor charging is controlled according a charging without delay mode after decreased intrinsic heart rate criteria are met and the potential need for a pacing pulse is relatively higher. In some examples, control circuit 80 may monitor one or more signals from sensors 90 in addition to or alternatively to the intrinsic cardiac electrical events sensed by sensing circuit 86 for determining if increased intrinsic heart rate criteria and/or decreased intrinsic heart rate criteria are met at blocks 104 and 108, respectively.

Figure 7:
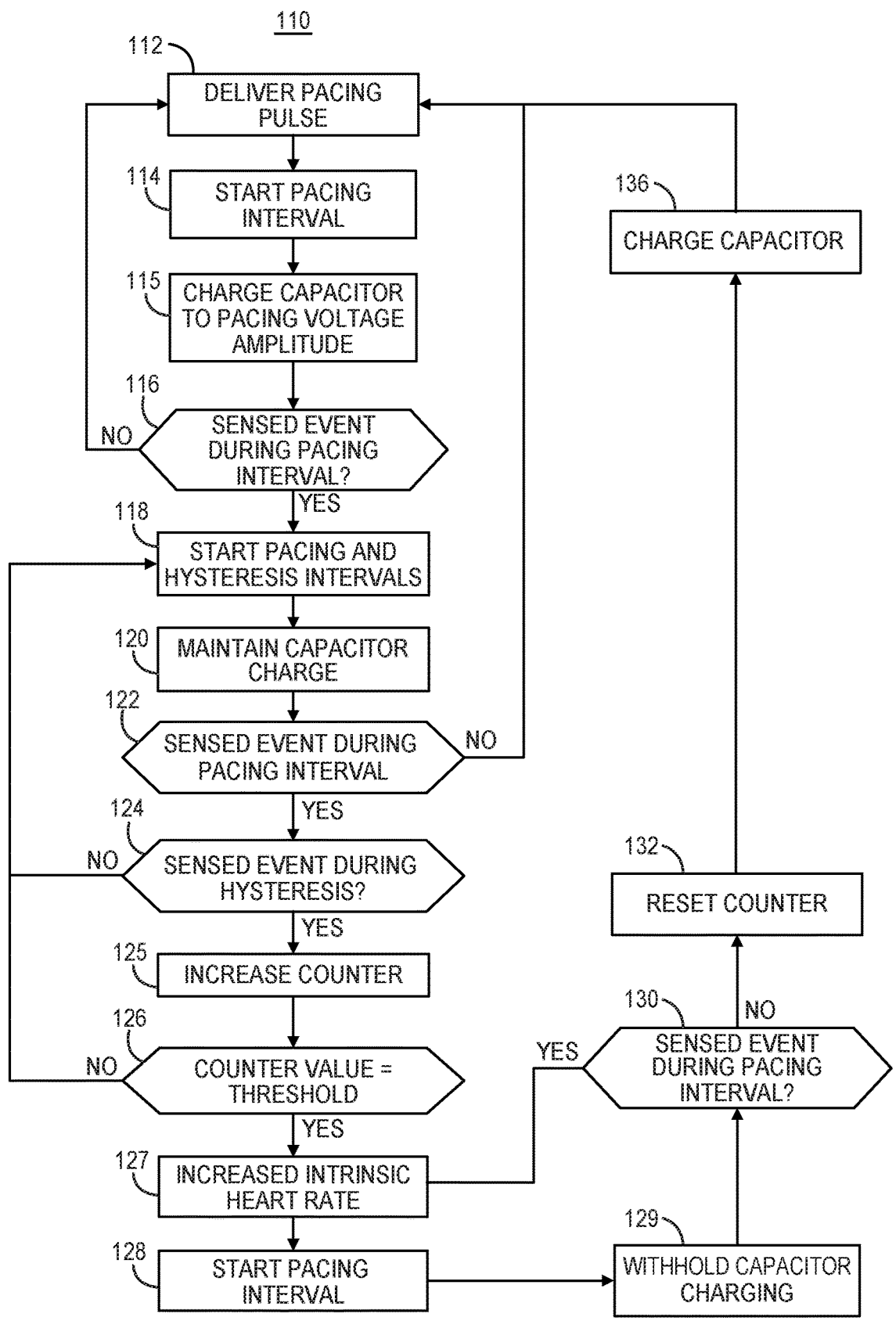
FIG. 7 is a flow chart of a method for controlling holding capacitor charging based on intrinsic heart rate criteria according to one example.

FIG. 7 is a flow chart 110 of a method for controlling holding capacitor charging based on intrinsic heart rate criteria according to one example. The method of FIG. 7 may be implemented for delivering a pacing therapy by either HV therapy circuit 83 or LV therapy circuit 85. The method of flow chart 110 controls the timing of holding capacitor charging, which may be HV holding capacitor 162 of HV therapy circuit 83 or one or more of the LV holding capacitors 352, 354, 356, or 358 of LV therapy circuit 85 depending on which of HV therapy circuit 83 or LV therapy circuit 85 is selected for delivering the pacing therapy.

At block 112, a pacing pulse is delivered by the selected HV therapy circuit 83 or LV therapy circuit 85. The pacing pulse is delivered upon expiration of a pacing interval, which may be a ventricular pacing interval during VVI pacing or another pacing interval according to another pacing therapy or pacing mode. Control circuit 80 restarts the pacing interval at block 114 in response to delivery of the pacing pulse. Control circuit 80 controls the charging circuitry of the selected HV therapy circuit 83 or LV therapy circuit 85 to charge the holding capacitor(s) back up to the pacing voltage amplitude at block 115 during the pacing interval without delay. In this way, if the pacing interval expires without a sensed event, the therapy circuit 83 or 85 is prepared to deliver the next pacing pulse upon pacing interval expiration.

At block 116, the control circuit 80 waits for the pacing interval to expire. If the pacing interval expires without sensing circuit 86 sensing an intrinsic cardiac event, e.g., an R-wave, at block 116, the scheduled pacing pulse is delivered in response to the expired pacing interval at block 112. Control circuit 80 restarts the pacing interval at block 114.

If sensing circuit 86 does sense an intrinsic cardiac event during the pacing interval at block 118, a sensed event signal may be passed from sensing circuit 86 to control circuit 80. In response to receiving the sensed event signal, e.g., an R-wave sensed event signal, from sensing circuit 86 before the pacing interval expires ("yes" branch of block 116), control circuit 80 inhibits the scheduled pacing pulse by re-starting the pacing interval at block 118.

Control circuit 80 may be configured to monitor for an increased intrinsic heart rate that is a predetermined rate greater than the programmed pacing rate for controlling capacitor charging mode switching. In one example, control circuit 80 may detect an increase in the intrinsic heart rate by starting a hysteresis interval at block 118 at the same time that the pacing interval is started. The hysteresis interval may be set equal to or shorter than the pacing interval. For instance, the hysteresis interval may be at least 10 to 30 ms shorter than the pacing interval. In this way, detection of an increased intrinsic heart rate for switching to a delayed capacitor charging mode may require a higher intrinsic heart rate than the intrinsic heart rate required to withhold pacing.

In one example the hysteresis interval is 15 ms shorter than the pacing interval when the pacing interval is 1 second, corresponding to a pacing rate of 60 pulses per minute. The hysteresis interval of approximately 0.985 ms corresponds to a heart rate of 65 beats per minute, about 5 pulses per minute faster than the pacing rate. The hysteresis interval may be determined by control circuit 80 as a fixed interval less than the pacing interval currently in effect. In other examples, control circuit 80 may determine the hysteresis interval by determining a sensed event interval corresponding to an intrinsic heart rate that is a fixed rate less than the pacing rate currently in effect, e.g., 5 to 15 beats less than the current pacing rate. In other examples, the hysteresis interval may be the same as the pacing interval.

Control circuit 80 may control the therapy delivery circuit 84 to maintain the charge of the holding capacitor at the programmed pacing voltage amplitude at block 112 after inhibiting the scheduled pacing pulse. The capacitor charge may be monitored during the pacing interval set in response to a sensed event, and if the charge drops more than a voltage tolerance below the pacing voltage amplitude, the charge of the holding capacitor may be topped off back to the pacing voltage amplitude.

Different protocols or techniques may be used to control topping off or maintaining the capacitor charge during pacing intervals. In one example, when LV therapy circuit 85 is used to deliver pacing pulses, one or more LV holding capacitors may be charged to the pacing voltage amplitude at the start of each pacing interval. In some cases, charging to the pacing voltage amplitude is controlled by charging to the pacing voltage amplitude plus a tolerance, e.g., to 110% to 115% of the programmed pacing voltage amplitude. In one example, the LV holding capacitor(s) used for delivering a pacing pulse are charged to 113% of the programmed pacing voltage amplitude at the start of each pacing interval that is reset in response to a delivered pacing pulse or sensed intrinsic event.

In other examples, for instance if the HV therapy circuit 83 is controlled to deliver pacing pulses, the HV holding capacitor 162 is charged to the pacing voltage amplitude (or the pacing voltage amplitude plus a tolerance), and continuous top-off charging is performed at block 120 until a pacing interval expires and a pacing pulse is delivered. In this example, processor and HV therapy control 152 may receive a capacitor charge signal from HV therapy circuit 83 indicating the voltage across HV holding capacitor 162, e.g., on each interrupt clock signal. Processor and HV therapy control 152 may compare the capacitor charge signal to a capacitor charge threshold and control HV charging circuit 154 to perform top-off charging following any interrupt clock signal during an unexpired pacing interval as needed to maintain the HV holding capacitor charge at the pacing voltage amplitude (plus or minus a specified tolerance). The specific protocol used to maintain a holding capacitor at the pacing voltage amplitude in a ready state for pacing pulse delivery may vary between devices but generally includes top-off charging to the pacing voltage amplitude (or the pacing voltage amplitude plus a tolerance) during each pacing interval as needed to maintain the holding capacitor charge at the pacing voltage amplitude.

If sensing circuit 86 does not sense an intrinsic event during the pacing interval started at block 118, "no" branch of block 122, control circuit 80 controls the therapy delivery circuit 84 to deliver the scheduled pacing pulse at block 112 in response to the expiration of the pacing interval. Control circuit 80 continues to charge the holding capacitor(s) according to the charging without delay mode during each pacing interval set in response to each delivered pacing pulse and sensed cardiac event.

If an intrinsic event is sensed by the sensing circuit 86 during the pacing interval started at block 118 ("yes" branch of block 122), control circuit 80 determines at block 124 if the sensed event occurred before the hysteresis interval expired. If the sensed event occurred after the hysteresis interval expired but before the pacing interval expired ("no" branch of block 124), the control circuit 80 inhibits the scheduled pacing pulse by restarting the pacing and hysteresis intervals at block 118. The holding capacitor charge is maintained at the pacing voltage amplitude at block 120 according the charging without delay mode.

If an intrinsic event is sensed by the sensing circuit 86 before the hysteresis interval expires ("yes" branch of block 124), control circuit 80 may increase the value of a counter at block 125. The counter may be previously initialized to zero and is used to count the number of cardiac cycles during which an intrinsic event is sensed prior to the expiration of the hysteresis interval. Control circuit 80 may be configured to detect an increased intrinsic heart rate based on a threshold number of cardiac cycles having a sensed event occurring during the hysteresis interval. If the counter has not reached the threshold number of cardiac cycles for detecting an increased intrinsic heart rate, "no" branch of block 126, control circuit 80 restarts the pacing and hysteresis intervals at block 118 and continues to maintain the charge of the holding capacitor at the pacing voltage amplitude in a ready state for pacing pulse delivery, according to the charging without delay mode.

If the counter reaches the threshold number of cardiac cycles having a sensed event during the hysteresis interval, as determined at block 126, control circuit 80 detects an increased intrinsic heart rate that is equal to or greater than the rate corresponding to the hysteresis interval. The threshold number of cardiac cycles having an intrinsic event sensed within the hysteresis interval required to detect an increased intrinsic heart rate may be one or more. In some examples, an intrinsic event may be required to be sensed within the hysteresis interval for at least five cardiac cycles in order to detect an increased intrinsic heart rate. The threshold number of cardiac cycles may be required to be consecutive in some examples, e.g., at least three consecutively sensed intrinsic events at or above the hysteresis rate corresponding to the hysteresis interval.

In other examples, the control circuit 80 may include an X of Y counter such that the cardiac cycles having intrinsic events sensed within respective hysteresis intervals may not be required to be consecutive, e.g., three out of five cardiac cycles, four out of six cardiac cycles, eight out of ten cardiac cycles or other ratio or percentage. In some examples, all Y cardiac cycles may be required to be sensed cardiac cycles with no paced cardiac cycles. For example, if four out of six cardiac cycles are required to include intrinsic events sensed within the hysteresis interval, the other two cardiac cycles may be required to include sensed intrinsic events within the pacing interval. None of the six cardiac cycles are paced cardiac cycles. In other examples, the Y cardiac cycles may include both paced and sensed cardiac cycles but at least X cardiac cycles are required to include a sensed intrinsic event during the hysteresis interval in order for an increased intrinsic heart rate to be detected.

At block 127, control circuit 80 determines that increased intrinsic heart rate criteria are met in response to the counter reaching the threshold number of cardiac cycles that each include an intrinsic sensed event during the respective hysteresis interval. In response to sensing the latest intrinsic event within the hysteresis interval that causes the increased intrinsic heart rate to be detected, the next scheduled pacing pulse is inhibited by restarting the pacing interval at block 128 without delivering a pacing pulse. Control circuit 80 switches to a delayed capacitor charging mode by not starting the hysteresis interval at block 128 and withholding capacitor charging at block 129. The holding capacitor charge is not maintained at the pacing voltage amplitude during the pacing interval after the heart rate has reached or exceeded the rate corresponding to the hysteresis interval for the threshold number of cardiac cycles.

If an intrinsic event is sensed by the sensing circuit 86 during the pacing interval started at block 128, as determined at block 130, control circuit 80 inhibits the scheduled pacing pulse by restarting the pacing interval at block 128 and continues to withhold capacitor charging at block 129. If the pacing interval expires at block 130 without an intrinsic event being sensed by the sensing circuit 86, the counter used to count the number of events within the hysteresis interval may be reset to zero at block 132. In response to the pacing interval expiring at block 130 without a sensed intrinsic event, control circuit 80 controls therapy delivery circuit 84 to charge the holding capacitor at block 130 and deliver the scheduled pacing pulse at block 112 as soon as the selected holding capacitor reaches the programmed pacing voltage amplitude. The time required to charge the holding capacitor(s) at block 136, after the pacing interval has expired, may delay the delivery of the pacing pulse at block 112. After the pacing pulse is delivered, the pacing interval is restarted at block 114, and the control circuit 80 controls the therapy delivery circuit 84 to charge the holding capacitor(s) during the pacing interval at block 115 according to the charging without delay mode.

In the example shown, expiration of the pacing interval a single time at block 130 during delayed capacitor charging mode may cause the control circuit 80 to return to the charging without delay mode for controlling charging of the holding capacitor(s) beginning at the start of the pacing interval after each pacing pulse or sensed event and maintaining the holding capacitor charge at the pacing voltage amplitude during the pacing interval as needed. In other examples, more than one pacing pulse may be required to be delivered due to an expired pacing interval during the delayed charging mode before reverting back to charging the holding capacitor without delay after each delivered pacing pulse. As a result, more than one pacing pulse may be delivered at a delayed time interval after expiration of the pacing interval due to the time required for charging the holding capacitor to the pacing voltage amplitude after expiration of the pacing interval.

After returning to block 112, maintaining the holding capacitor in a "ready" state by charging to the pacing voltage amplitude and topping off the charge as needed until a pacing interval expires may continue until an increased intrinsic heart rate is detected again. The increased intrinsic heart rate is detected according to predetermined criteria which may include a hysteresis interval and a required number of cardiac cycles having an intrinsic event sensed within the hysteresis interval, where the hysteresis interval may be shorter than the pacing interval.

Figure 8A:
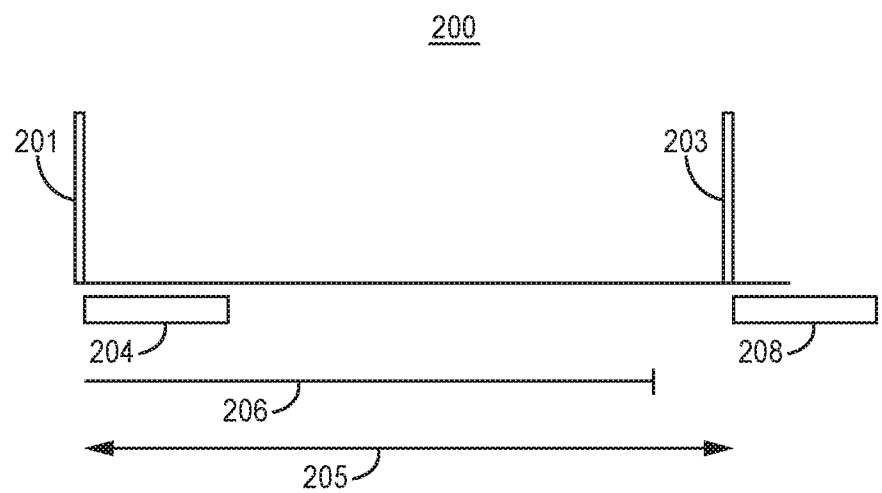
FIGS. 8A through 8D are timing diagrams depicting operations performed by an ICD in controlling holding capacitor charging based on the timing of sensed intrinsic events.

FIGS. 8A through 9C are timing diagrams depicting operations performed by ICD 14 in controlling holding capacitor charging based on the timing of sensed intrinsic events. FIGS. 8A and 8B are timing diagrams depicting operations performed by ICD 14 during the capacitor charging without delay mode. In FIG. 8A, timing diagram 200 shows two pacing pulses 201 and 203 delivered by ICD 14 separated in time by a pacing interval 205. During pacing, control circuit 80 may control therapy delivery circuit 84 to charge a holding capacitor during each pacing interval, until increased intrinsic heart rate criteria are met, which may be based on a hysteresis interval 206 shorter than the pacing interval 205.

Upon delivering pacing pulse 201, therapy delivery circuit 84 may be controlled to charge the holding capacitor(s) used for delivering pacing pulse 201 during a capacitor charging time 204, according to the charging without delay mode. As described above, the capacitor charged during charging time 204 may be the HV holding capacitor 162 (FIG. 4) or any combination of LV holding capacitors 352, 354, 356, and/or 358 (FIG. 5). The charging time 204 is not necessarily a fixed time interval. Rather the charging time 204 is the time required to recharge the holding capacitor(s) back to the pacing voltage amplitude after pacing pulse 201 is delivered and will depend on the pacing voltage amplitude, the residual charge left on the holding capacitor after pacing pulse delivery, the capacitance of the holding capacitor, and other factors. While charging time 204 is shown as a single discrete time interval at the beginning of pacing interval 206, it is recognized that the capacitor charge may be monitored throughout pacing interval 205 and topped off as needed if the capacitor charge decreases below the pacing voltage amplitude due to leakage current in the ICD circuitry. The charging time 204 represented as a block of time is intended to represent the capacitor charging without delay mode, which may include charging at the beginning and/or throughout the pacing interval as needed to recharge the holding capacitor to the pacing voltage amplitude during the pacing interval.

Pacing interval 205, which may be a VV interval during VVI pacing for example, is started upon delivery of the first pacing pulse 201. If no intrinsic events are sensed during the pacing interval 205, pacing pulse 203 is delivered by therapy delivery circuit 84 in response to the expiration of pacing interval 205. The holding capacitor is recharged during charging time 208 following pacing pulse 203 according to the charging without delay mode.

Figure 8B:
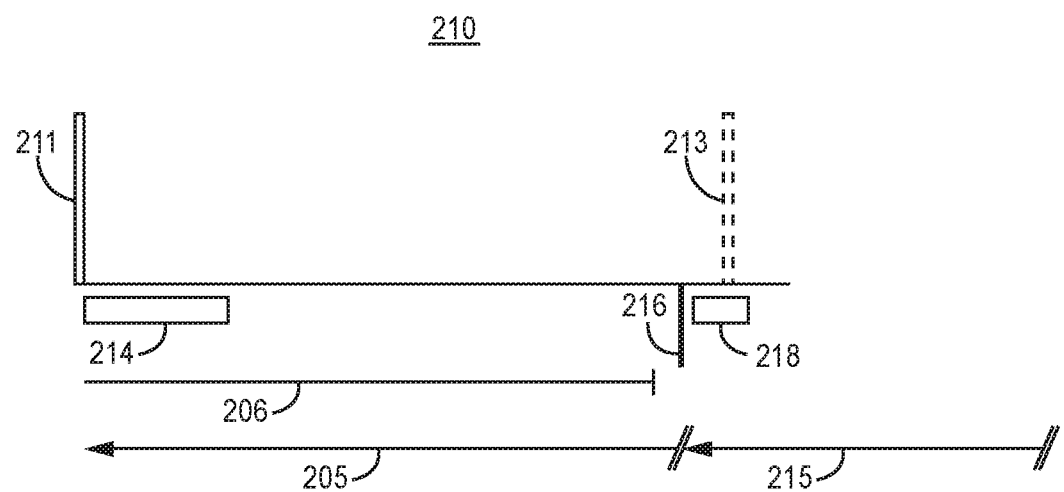

FIG. 8B is a timing diagram 210 showing inhibition of a pacing pulse in response to a sensed intrinsic event during the pacing interval 205. Pacing pulse 211 is delivered, and the holding capacitor is recharged to the pacing voltage amplitude during pacing interval 205 without delay, as indicated capacitor charging time 214. If an intrinsic event is sensed during the pacing interval 205, the scheduled pacing pulse 213 is withheld (as indicated by dashed line). Sensing circuit 86 may be configured to produce a sensed event signal 216, e.g., an R-wave sensed event signal, that is passed to control circuit 80. In response to the sensed event signal 216, the pacing interval 205 is restarted as new pacing interval 215, inhibiting the scheduled pacing pulse 213.

The control circuit 80 may monitor the charge of the holding capacitor and top off the capacitor charge during recharging time 218 if needed to maintain the holding capacitor voltage at the pacing voltage amplitude (or within a specified tolerance voltage of the pacing voltage amplitude) during the pacing interval 215. The sensed event signal 216 that is within the pacing interval 205 but not within the hysteresis interval 206 does not alter the control of capacitor charging in this example. The holding capacitor continues to be recharged during each pacing interval 205 (or 215) as needed according to the charging without delay mode in order to prepare and maintain the holding capacitor at the pacing voltage amplitude. The holding capacitor may be charged during pacing interval 205 following a pacing pulse 211 as well as during a pacing interval 215 following a sensed event signal 216 if charging is needed to top off the capacitor charge to the pacing voltage amplitude. Even though a pacing pulse has not been delivered, the holding capacitor charge may fall below the pacing voltage amplitude due to inherent leakage current in the ICD circuitry. Top off capacitor charging may not be required immediately following every sensed event. Control circuit 80 may be configured to monitor the holding capacitor voltage at the start of each pacing interval and/or throughout each pacing interval, start charging if the voltage is less than a tolerance below the pacing voltage amplitude, and terminate charging when the charge is back up to the pacing voltage amplitude.

If the intrinsic heart rate is less than a hysteresis rate corresponding to hysteresis interval 206 but greater than the pacing rate corresponding to pacing interval 205, the holding capacitor charge continues to be monitored and maintained at the pacing voltage amplitude according to the charging without delay mode. As such, if the sensed event signal 216 occurs after expiration of the hysteresis interval 206, capacitor charging is performed as needed without delay.

Figure 8C:
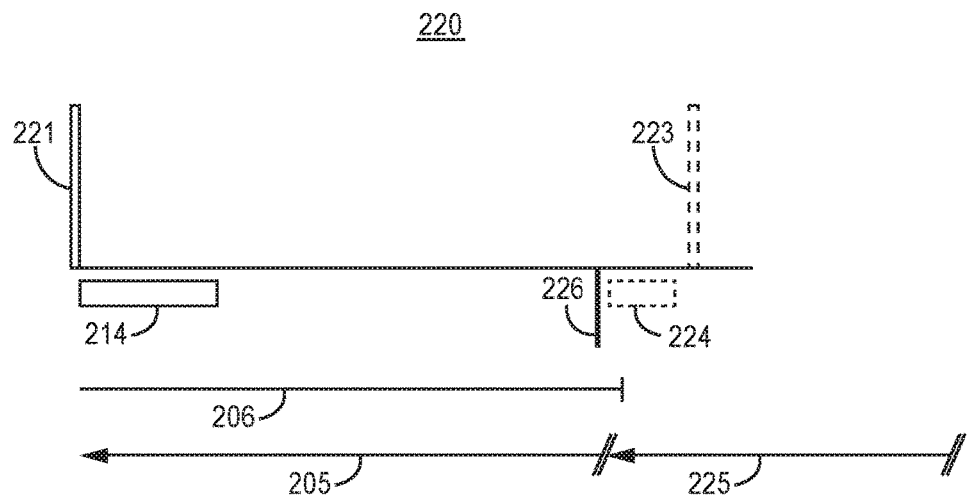
Figure 8D:
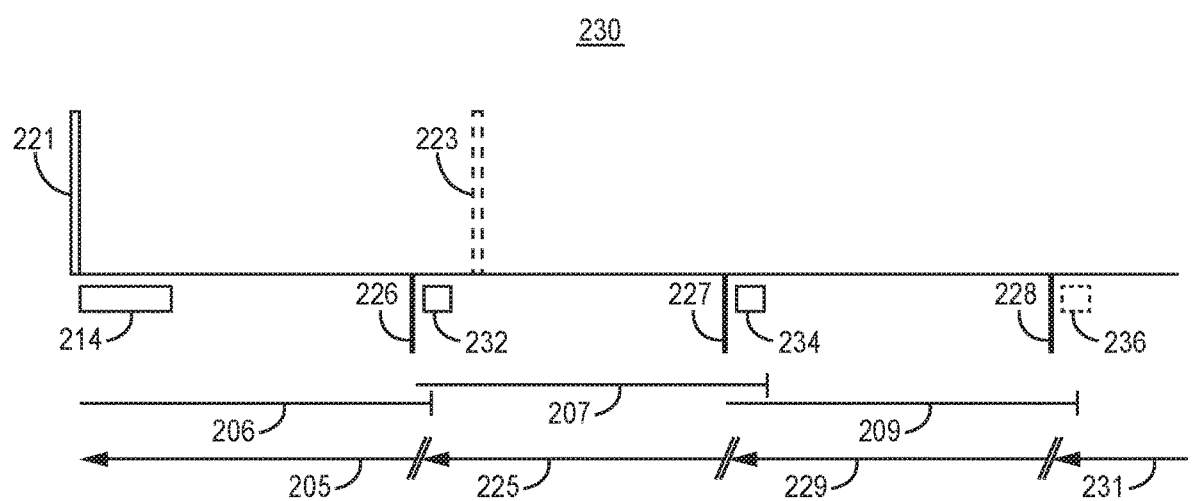

FIGS. 8C and 8D are timing diagrams depicting operations of ICD 14 performed for switching from the charging without delay mode to the delayed charging mode in response to increased intrinsic heart rate criteria being met. FIG. 8C is a timing diagram showing pacing pulse 221 followed by capacitor charge time 214 according to the charging without delay mode. The pacing interval 205 and the hysteresis interval 206 are started simultaneously in response to the delivered pacing pulse 221. The next scheduled pacing pulses 223 is inhibited due to a sensed intrinsic event signal 226 that is received from sensing circuit 86 by control circuit 80 during pacing interval 205. The pacing interval 205 is restarted as new pacing interval 225 in response to sensed event signal 226.

During the charging without delay mode, control circuit 80 may monitor for an increase in heart rate, faster than the pacing rate corresponding to pacing interval 205, by counting the number of cardiac cycles having an intrinsic event sensed during the hysteresis interval 206. In the example shown, control circuit 80 detects an increased intrinsic heart rate in response to the sensed event signal 226 occurring within hysteresis interval 206. Control circuit 80 switches from the charging without delay mode to the delayed charging mode in response to detecting the increased intrinsic heart rate by withholding capacitor charging during the next pacing interval 225.

This withholding of capacitor charging is illustrated schematically by dashed capacitor charging time block 224, during which no capacitor charging actually occurs. If the sensed event signal 226 had occurred after hysteresis interval 206 as described in conjunction with FIG. 8B, capacitor charging time 224 would occur during pacing interval 225 as needed to maintain the holding capacitor charge at the pacing voltage amplitude. Capacitor charging may be withheld during pacing interval 225 by withholding monitoring of the capacitor charge during the pacing interval 225 or by withholding charging even when the capacitor charge falls below the pacing voltage amplitude. In the example of FIG. 8C, a sensed event signal 226 during a single hysteresis interval 206 is shown to cause control circuit 80 to switch from charging without delay to the delayed capacitor charging mode and withhold capacitor charging. In other examples, a sensed event signal during each of more than one respective hysteresis interval as described above in conjunction with FIG. 7 may be required for increased intrinsic heart rate criteria to be met to cause switching to the delayed charging mode. For instance, sensed event signal 226 may be the Xth event sensed within a respective number of X hysteresis intervals out of Y cardiac cycles, causing the increased intrinsic heart rate criteria to be met.

FIG. 8D is a timing diagram 230 depicting operations performed by ICD 14 in controlling holding capacitor charging in response to detecting an increased heart rate based on hysteresis interval 206 according to another example. In the example of FIG. 8D, three consecutive sensed event signals 226, 227 and 228 are required to each be sensed within a respective hysteresis interval 206, 207 and 209 in order to detect an increased intrinsic heart rate and switch the capacitor charging mode to the delayed charging mode. Each hysteresis interval 206, 207 and 209 is started in response to the preceding cardiac event, pacing pulse 221, sensed event signal 226 and sensed event signal 227, respectively. In this example, criteria for detecting an increased intrinsic heart rate is not met until the three consecutively sensed events 226, 227 and 228 are sensed within the hysteresis interval 206, 207 and 208 set for the respective cardiac cycles. As such, control circuit 80 does not withhold or delay capacitor charging until the increased heart rate detection criteria are satisfied. Control circuit 80 controls the charging circuitry of therapy delivery circuit 84 to charge the holding capacitor(s) used for generating pacing pulses to the pacing voltage amplitude as needed during each of pacing intervals 225 and 229 started in response to sensed event signals 226 and 227 even though the sensed event signals 226 and 227 each occurred above the hysteresis rate, within respective hysteresis intervals 206 and 207.

Recharging of the holding capacitor(s) may occur during charging times 232 and 234 at the beginning of the respective pacing intervals 225 and 229 or throughout the pacing intervals 225 and 229 as needed to top-off the holding capacitor charge within a tolerance of the pacing voltage amplitude. It is recognized, that depending on the duration of the pacing interval, the inherent leakage current and other factors, recharging of the holding capacitor(s) may not be required during every pacing interval in order to maintain the capacitor charge within a specified tolerance of the pacing voltage amplitude. However, control circuit 80 may monitor or check the charge of the holding capacitor during each pacing interval 225 and 229 that is started in response to the sensed event signals 226 and 227, respectively, until criteria for detecting an increase in heart rate are satisfied.

Upon detecting the third sensed event signal 228 within hysteresis interval 209, an increased intrinsic heart rate that is faster than or equal to the hysteresis rate is detected in this example. In response, control circuit 80 switches to the delayed charging mode by withholding capacitor charging during the next pacing interval 231. The HV or LV charging circuit of therapy delivery circuit 84 being used for pacing pulse generation may be turned "off" by withholding power supplied to the charging circuit for charging the holding capacitor. Withholding of capacitor charging is illustrated by the dashed box 236. No charging occurs following sensed event signal 228 during the first pacing interval 231 after increased intrinsic heart rate criteria are met. Monitoring of the holding capacitor voltage, e.g, by a comparator comparing the capacitor voltage to the programmed pacing voltage amplitude, that may normally be performed to control topoff charging of the holding capacitor during a pacing interval may be disabled in response to detecting the increased heart rate since no charging of the holding capacitor is performed again until at least one pacing interval expires or until other decreased intrinsic heart rate criteria are subsequently satisfied.

Figure 9A:
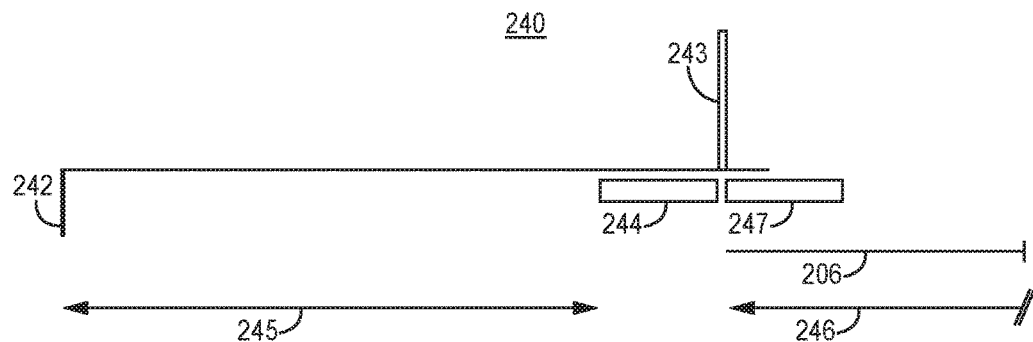
FIGS. 9A-9C are timing diagrams depicting operations performed by an ICD or pacemaker for withholding capacitor charging according to a delayed capacitor charging mode and switching back to a charging without delay.
Figure 9B:
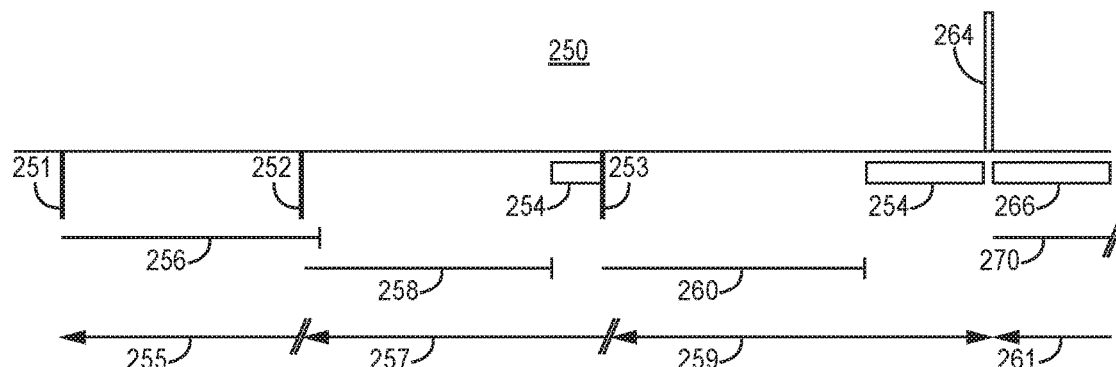
Figure 9C:
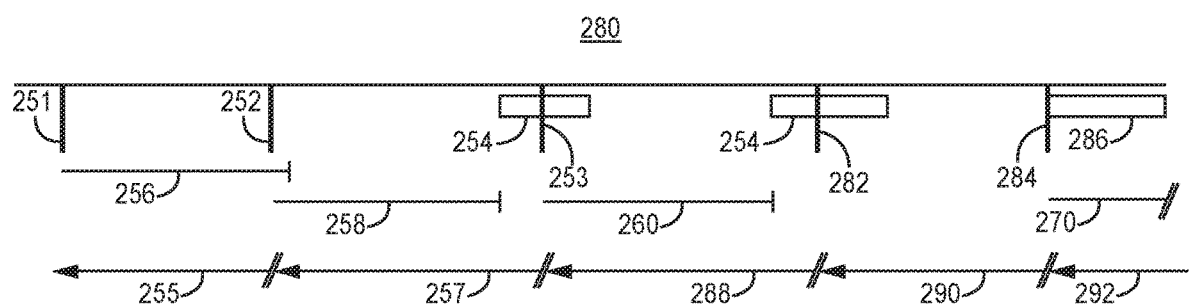

FIGS. 9A-9C are timing diagrams depicting operations performed by ICD 14 for withholding capacitor charging according to a delayed capacitor charging mode and switching back to the charging without delay mode in response to decreased intrinsic heart rate criteria being met. Holding capacitor charging is withheld after increased intrinsic heart rate criteria are met as described above in conjunction with FIGS. 8C and 8D. As shown in FIG. 9A, the pacing interval 245 is started in response to a sensed event signal 242. No capacitor charging is performed during pacing interval 245 because capacitor charging is being withheld according to the delayed charging mode due to increased intrinsic heart rate criteria being previously met. Pacing interval 245 expires without a sensed intrinsic event. Control circuit 80 controls therapy delivery circuit 84 to charge the holding capacitor(s) in response to the pacing interval 245 expiring as indicated by charging time 244. Once the holding capacitor voltage has reached the pacing voltage amplitude, pacing pulse 243 is delivered. Pacing pulse 243 may be delivered at a delay after the expiration of pacing interval 245 that is equal to the charging time 244 required to charge the holding capacitor up to the pacing voltage amplitude.

Control circuit 80 may be configured to detect a decreased intrinsic heart rate in response to expiration of a single pacing interval 245 without as sensed intrinsic event. In response to detecting the decreased heart rate that is slower than the pacing rate based on no intrinsic event being sensed during the pacing interval 245, the control circuit 80 switches to charging without delay by charging the holding capacitor during each pacing interval as needed to maintain the holding capacitor(s) in a ready state for pacing pulse delivery. Pacing interval 246 is started in response to delivering pacing pulse 243. Capacitor charging may be initiated at the beginning or onset of pacing interval 246 after detecting a decreased intrinsic heart rate based on at least one expired pacing interval 245. Control circuit 80 may control the therapy delivery circuit 84 to recharge the holding capacitor to the pacing voltage during charging time 247 following pacing pulse 243.

In addition to starting pacing interval 246, control circuit 80 may start hysteresis interval 206 to begin monitoring for an increased intrinsic heart rate as described above in conjunction with FIGS. 8C-8D. Control circuit 80 continues to charge the holding capacitor(s) during each pacing interval as needed according to the charging without delay mode in order to maintain the capacitor charge within a specified tolerance of the pacing voltage amplitude during each pacing interval until an increased intrinsic heart rate is detected. Control circuit 80 may enable power source 98 to provide power to the HV therapy circuit 83 or LV therapy circuit 85 for charging selected holding capacitor(s) until an increased intrinsic heart rate is detected. Control circuit 80 may compare a capacitor charge signal from the selected HV therapy circuit 83 or LV therapy circuit 85 at the start of pacing interval 246 and each pacing interval thereafter until an increased intrinsic heart rate is detected again. If the capacitor charge signal indicates that the holding capacitor charge is less than a tolerance below the pacing voltage amplitude, control circuit 80 enables charging of the selected holding capacitor(s) as needed during pacing interval 246.

In FIG. 9A, the decreased intrinsic heart rate is detected by control circuit 80 in response to a single expired pacing interval for the purposes of switching back to charging without delay. In other examples, more than one expired pacing interval may be required for detecting a decreased intrinsic heart rate to cause control circuit 80 to change the timing of capacitor charging. For example, capacitor charging may occur upon expiration of the pacing interval for two or more pacing cycles resulting in pacing pulses being delivered at the pacing interval plus a delay interval equal to the required charging time for the two or more pacing cycles. A decreased intrinsic heart rate may be detected in response to a predetermined number of consecutive or non-consecutive (X out of Y) expired pacing intervals.

To illustrate, if a decreased intrinsic heart rate is detected in response to three consecutively expired pacing intervals, up to three pacing pulses may be delivered at a rate less than the pacing rate corresponding to pacing interval 245. The actual pacing rate for the first three pacing pulses may be the rate corresponding to the pacing interval 245 plus the charging time 244 required to charge the holding capacitor to the pacing voltage amplitude. For instance, the pacing interval 245 may be set to 1.5 seconds for a lower pacing rate of 40 pulses per minute. The charge time 244 may average 0.5 seconds, resulting in an actual pacing rate of 30 pulses per minute for the three pacing cycles leading up to satisfaction of the decreased heart rate detection criteria. After the third pacing pulse, the control circuit 80 may detect a decreased intrinsic heart rate based on decreased heart rate criteria and re-enable the therapy delivery circuit 84 to charge the holding capacitor during each pacing interval without delay so that subsequent pacing pulses are each delivered at the expiration of the programmed pacing interval without delay In some instances, a sensed event signal could be received by control circuit 80 during the charging time 244. In this case, the pacing pulse 243 would be inhibited and capacitor charging could be terminated or allowed to continue. If a required number of expired pacing intervals has been reached for decreased intrinsic heart rate criteria to be met, control circuit 80 may switch back to the charging without delay mode even if a sensed event signal was received during the charging time, after the pacing interval expired, causing the pacing pulse to be inhibited. As such, a required number of pacing intervals for detecting a decreased intrinsic heart rate may be reached without requiring the same number of delivered pacing pulses. The number of delivered pacing pulses may be less than the number of expired pacing intervals due to sensed event signals being received during the capacitor charging.

FIG. 9B is a timing diagram of a method for controlling holding capacitor charging during a decreasing intrinsic heart rate according to another example. In some examples, capacitor charging is withheld for the entire pacing interval according to the delayed capacitor charging mode, as shown in FIG. 9A. In other examples, capacitor charging is withheld for a portion of the pacing interval but may be started during the pacing interval after a charging delay interval. In the example of FIG. 9B, a capacitor charging delay interval 256 is set in response to sensed event signal 251, along with starting pacing interval 255. In response to detecting an increased heart rate based on the hysteresis interval as described above in conjunction with FIG. 8C or 8D, control circuit 80 may withhold capacitor charging during the pacing interval 255 until after the capacitor charging delay interval 256 expires, according to the delayed charging mode. If a sensed event 252 occurs during the capacitor delay interval 256, holding capacitor charging is withheld and the capacitor charging delay interval is restarted as interval 258. The pacing interval is restarted as interval 257 in response to the sensed event signal 252.

Charging delay interval 258 expires before the next sensed event signal 253. Capacitor charging is initiated as indicated by charging time 254 in response to charging delay interval 258 expiring. In response to receiving a sensed event signal 253, capacitor charging 254 may be terminated since the scheduled pacing pulse is inhibited and the pacing interval is restarted as pacing interval 259. In other examples, charging to the pacing voltage amplitude may be completed during charging time 254 (which may extend past sensed event signal 253 and into the next pacing interval 259). The next charging delay interval 260 is started along with the pacing interval 259 in response to the sensed event signal 253.

If charging delay interval 260 expires, control circuit 80 is configured to control the therapy delivery circuit 80 to initiate capacitor charging 254. If the pacing interval 259 expires, pacing pulse 264 is delivered. A new pacing interval 261 is started and a hysteresis interval 270 may be set in response to delivered pacing pulse 264 for use in detecting an increased intrinsic heart rate again as described above, e.g., in conjunction with FIG. 7C or 7D. In some instances, pacing pulse 264 may be delivered upon pacing interval expiration without delay if the holding capacitor is fully charged to the pacing voltage amplitude by the time the pacing interval 259 expires. In other instances, capacitor charging may be incomplete upon expiration of pacing interval 259, and pacing pulse 264 may be delivered at a short delay after expiration of the pacing interval 259 as required to complete capacitor charging.

In some examples, control circuit 80 may be configured to determine an estimated capacitor charging time based on the pacing voltage amplitude and capacitance of the holding capacitor. In other examples, control circuit 80 may be configured to determine the capacitor charging time based on charging history. For instance, the time interval from the start of capacitor charging following a delivered pacing pulse until a charge completion signal is received from the therapy delivery circuit 84 may be determined by control circuit 80. This time interval, e.g., charging interval 247 of FIG. 9A, or an average of multiple charge completion time intervals obtained in this manner during multiple capacitor charging occurrences, may be determined as the capacitor charging time.

Control circuit 80 may be configured to set the capacitor charging delay interval 260 based on the pacing interval 259 and the calculated or measured capacitor charging time. The capacitor charging delay interval 260 may be determined as the difference of the pacing interval 259 and the determined capacitor charging time. In some examples, the capacitor charging delay interval 260 may be the difference between pacing interval 259 and the determined capacitor charging time less a pacing safety interval (which may be set to zero) to promote charge completion prior to expiration of pacing interval 259 to avoid any delay of pacing pulse 264.

In the example shown in FIG. 9B, control circuit 80 controls the therapy delivery circuit 84 to recharge the holding capacitor during charging time 266 after delivery of pacing pulse 264. Expiration of a single pacing interval 259 may cause control circuit 80 to switch to the charging without delay mode to restore the holding capacitor charge to the pacing voltage during each pacing interval without waiting for a capacitor charging delay interval to expire. In other examples, a predetermined number of pacing intervals may be required to expire before reverting back to charging without delay during each pacing interval. For instance, charging may be performed after the capacitor charging delay interval after two or more consecutive or non-consecutive pacing pulses, e.g., after 3 consecutive pacing pulses or after 3 pacing pulses out of 5 consecutive cardiac cycles, before switching to charging without delay, without setting the capacitor charging delay interval.

FIG. 9C is a timing diagram of another example for controlling holding capacitor charging during a decreasing intrinsic heart rate. In the example of FIG. 9B, control circuit 80 detects a decreased intrinsic heart rate based on a predetermined number of expired pacing intervals. In other examples, control circuit 80 may be configured to detect a decreased intrinsic heart rate in response to a predetermined number of expired capacitor charging delay intervals. The decreased intrinsic heart rate detection criteria may be determined to be satisfied based on expired capacitor charging delay intervals, even if no pacing intervals have expired.

As shown in FIG. 9C and described above in conjunction with FIG. 9B, a sensed event 252 during a capacitor charging delay interval 256 causes capacitor charging to be withheld. Expiration of a capacitor charging intervals 258 and 260 without sensed intrinsic events results in capacitor charging 254 to top off the holding capacitor charge at the pacing voltage amplitude. In the example of FIG. 9B, capacitor charging 254 was terminated in response to a sensed event signal 253 during the capacitor charging. In the example of FIG. 9C, capacitor charging 254 continues after sensed event signal 253 to complete charging to the pacing voltage amplitude.

Sensed events 253 and 282 during the capacitor charging 254 and prior to expiration of respective pacing intervals 257 and 288 cause scheduled pacing pulses to be inhibited. In response to the expiration of a predetermined number of charging delay intervals, two in this example (258 and 260), control circuit 80 detects a decreased intrinsic heart rate and switches the capacitor charging mode to charging without delay after sensed event signal 282. A capacitor charging delay interval is not started concomitantly with pacing interval 290. Capacitor charging may be completed as needed to top-off the capacitor charge following sensed event 282 and during the subsequent pacing interval 290. The next event is a sensed event 284 during pacing interval 290. Capacitor charging occurs without delay during pacing interval 292 as indicated by charge time 286. A hysteresis interval 270 may be started following the sensed event 284 concomitantly with pacing interval 292 to facilitate detection of increased intrinsic heart rate criteria being satisfied.

In this example, if a sensed intrinsic event occurs during the capacitor charging delay interval, charging is withheld because the intrinsic heart rate is faster than the rate corresponding to the capacitor charging delay interval. If a predetermined number of capacitor charging delay intervals expire, however, the intrinsic heart rate may be decreasing toward a potential need for pacing. The control circuit 80 may detect a decreased intrinsic heart rate in response to a predetermined number of expired capacitor charging delay intervals and switch to charging without delay in response to detecting the decreased intrinsic heart rate. As such, switching to capacitor charging without delay may occur before the intrinsic heart rate falls below the programmed pacing rate and before any pacing pulses are delivered.

Figure 10:
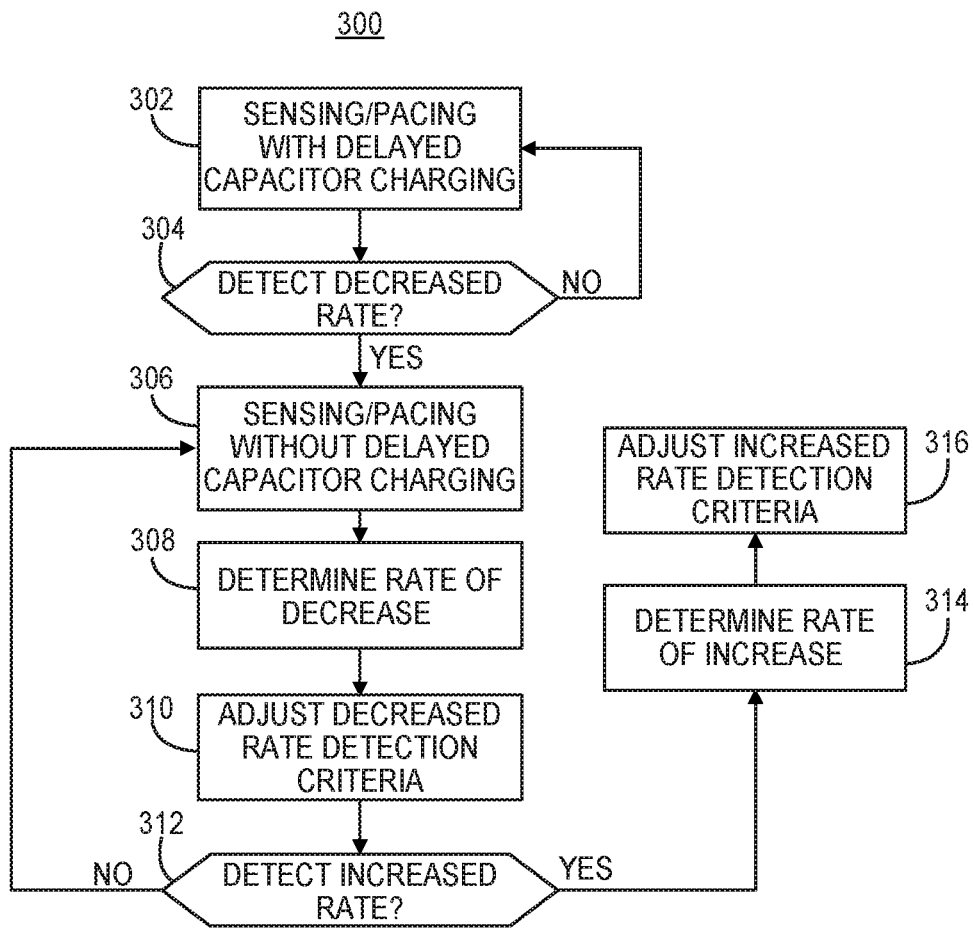
FIG. 10 is a flow chart of a method for controlling capacitor charging according to yet another example.

FIG. 10 is a flow chart 300 of a method for controlling holding capacitor charging according to another example. At block 302, control circuit 80 controls the therapy delivery circuit 84 to charge the selected holding capacitor(s) for delivering pacing pulses after a capacitor charging delay interval, which may be equal to or less than the pacing interval currently being used for scheduling a pacing pulse. Operations performed at block 302 may include determination of a calculated or measured capacitor charge completion time interval used for setting the capacitor charging delay interval. Control circuit 80 withholds capacitor charging in response to receiving a sensed event signal during the capacitor charging delay interval, and the scheduled pacing pulse is inhibited, e.g., as shown in FIGS. 9B and 9C. The capacitor charging delay interval and the pacing interval are restarted. In other examples, the pacing interval is restarted after each pacing pulse and sensed event signal and capacitor charging is delayed until a pacing interval expires without setting a separate capacitor charging delay interval, e.g., as in FIG. 9A.

Control circuit 80 may detect a decreased intrinsic heart rate at block 304 based on a threshold number of expired pacing intervals, e.g., as in FIGS. 9A and 9B. The number of expired pacing intervals may be greater than the number of delivered pacing pulses since a sensed event after the pacing interval expiration may occur during delayed charging, causing the pacing pulse to be inhibited. In other examples, control circuit 80 may detect a decreased intrinsic heart rate in response to a predetermined number of expired charging delay intervals, e.g., as shown in FIG. 9C. In response to detecting the decreased intrinsic heart rate, control circuit 80 switches to controlling the therapy delivery circuit 84 to charge the holding capacitor used for pacing without delay at block 306, e.g., without setting the capacitor charging delay interval. Re-charging or top-off charging to maintain the holding capacitor charge at the pacing voltage amplitude during the pacing interval may occur at the beginning of a pacing interval or throughout the pacing interval set after a delivered pacing pulse or sensed event.

At block 308, control circuit 80 may determine the rate or slope of the decrease in the intrinsic heart rate. For example, the control circuit 80 may determine the rate of decrease over a predetermined number of heart beats or a predetermined time interval leading up to the time at which the decreased heart rate criteria were satisfied. If the heart rate decrease occurs abruptly, the decreased intrinsic heart rate detection criteria may be adjusted at block 310 to enable detection of the decreased heart rate in fewer cardiac cycles, e.g., as few as one cardiac cycle. If the rate of decrease is relatively slow, the decreased intrinsic heart rate detection criteria may be adjusted at block 310 by increasing the number of expired capacitor charging delay intervals and/or expired pacing intervals required to detect the decreased intrinsic heart rate before switching from delayed capacitor charging to charging the holding capacitor(s) without delay.

Control circuit 80 continues to control the therapy delivery circuit 84 to charge the holding capacitor without delay during each pacing interval to maintain the holding capacitor in a ready state until an increased intrinsic heart rate is detected at block 312. As described above, criteria for detecting an increased intrinsic heart rate may require one or more cardiac cycles having a sensed event signal occurring within the hysteresis interval.

When increased intrinsic heart rate criteria are met at block 312, control circuit 80 may be configured to determine the rate or slope of the increase in the intrinsic heart rate at block 314. The rate of increase may be determined over a pre-determined time interval or number of cardiac cycles. Based on the rate of increase, control circuit 80 may adjust the criteria for detecting the increased intrinsic heart rate at block 316. If the rate of increase occurs rapidly, the control circuit may set a relatively low number of sensed events occurring at or above the hysteresis interval rate as a requirement for detecting the increased intrinsic heart rate. Alternatively or additionally, the hysteresis interval may be set to a relatively longer interval, up to the pacing interval, to promote earlier detection of an increasing intrinsic heart rate. By adjusting the increased intrinsic rate criteria in a patient whose heart rate recovers rapidly, battery charge is conserved by switching back to delayed capacitor charging earlier.

If the rate of increase occurs gradually, e.g., with intermittent pacing and sensing or sensing near the pacing rate for a sustained time interval, the hysteresis interval may be adjusted to a relatively shorter interval and/or the required number of sensed hysteresis interval events may be reduced. By adjusting the increased intrinsic rate detection criteria, switching back and forth between delayed capacitor charging and charging without delay may be avoided and any pacing delays due to delayed capacitor charging may be avoided while the heart rate is gradually increasing.

After adjusting the increased rate detection criteria based on the rate of increase, the control circuit 80 operates to control the therapy delivery circuit 84 to delay charging of the holding capacitor during pacing intervals following sensed events and pacing pulses. Capacitor charging is delayed by withholding capacitor charging until a pacing interval expires, e.g., as shown in FIG. 9A, or until a capacitor charging delay interval expires, e.g., as shown in FIG. 9B or 9C. Capacitor charging is delayed until a decreased intrinsic heart rate is detected according to adjusted decreased rate detection criteria. It is to be understood that while adjustment of both decreased rate detection criteria and increased rate detection criteria are indicated in FIG. 10 based on determining the respective rate of decrease and rate of increase of intrinsic heart rate changes, the control circuit 80 may be configured to automatically adjust only the decreased intrinsic heart rate detection criteria, adjust only the increased intrinsic heart rate detection criteria, both or neither.

Figure 11:
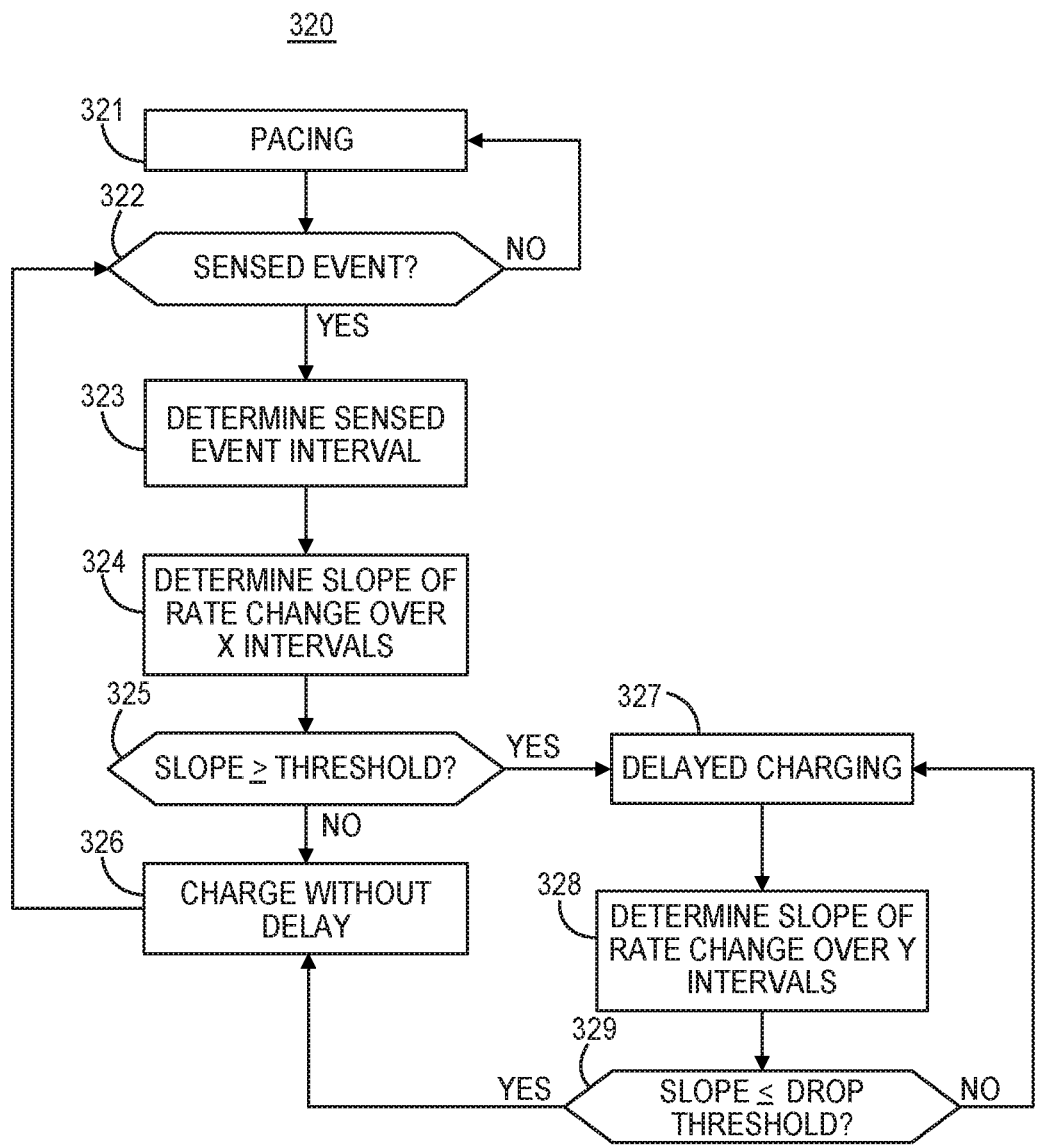
FIG. 11 is a flow chart of a method for controlling the capacitor charging mode based on the rate or slope of a change in heart rate.

FIG. 11 is a flow chart 320 of a method for controlling the capacitor charging mode based on the rate or slope of a change in heart rate. At block 321, ICD 14 may be delivering pacing pulses during a sustained run of pacing due to expired pacing intervals without sensed intrinsic events. The control circuit 80 is controlling the therapy delivery circuit 84 to charge the holding capacitor(s) without delay.

At block 322, an intrinsic event is sensed, causing a scheduled pacing pulse to be inhibited. The sensed event interval is determined at block 323. At block 324, the slope of the heart rate over a predetermined time interval or a predetermined number of cardiac cycles is determined. For example, five to ten of the most recent sensed event intervals may be used to determine the slope of the heart rate change at block 324. If the intrinsic heart rate is increasing rapidly, e.g., due to increased patient activity, capacitor charging may be withheld since the likelihood of a pacing interval expiring is now greatly reduced. Control circuit 80 compares the slope of the intrinsic heart rate change over the predetermined time interval or number of sensed intrinsic events to a threshold slope at block 325. This threshold slope is a positive slope corresponding to a relatively rapid rise in intrinsic heart rate.

If the required time interval or number of sensed event intervals for determining the slope at block 324 has not been reached, the slope of the intrinsic heart rate change will be less than the slope threshold at block 325. In that case, capacitor charging without delay continues at block 326. The process returns to block 322 to wait for the next sensed event.

If the required time interval or number of sensed event intervals has been reached to enable slope determination at block 324, but the slope is less than the slope threshold at block 325, the control circuit 80 continues to control capacitor charging without delay at block 326. The intrinsic heart rate may be increasing but may not be increasing rapidly enough or may not be increasing monotonically to justify switching from the charging without delay mode to the delayed charging mode. The probability of a pacing interval expiring is still high enough to warrant maintaining the holding capacitor in a ready state for pacing.

If the slope of the intrinsic heart rate change determined at block 324 is equal to or greater than the slope threshold at block 325, control circuit 80 switches the capacitor charging mode to delayed capacitor charging at block 327, e.g., by setting a capacitor charging delay interval as described previously or withholding capacitor charging during all or a portion of the next pacing interval. The slope threshold applied at block 325 may require that the intrinsic heart rate increase from the current pacing rate to 20 beats per minute faster than the pacing rate within one minute, for example, though other slope thresholds may be defined according to patient need.

After switching to delayed capacitor charging, the control circuit 80 may continue to monitor the slope of the intrinsic heart rate change at block 328. The slope may be compared to a rate drop threshold at block 329. The rate drop threshold may be applied to the slope of the intrinsic heart rate over a predetermined time interval or predetermine number (Y) of sensed event intervals to determine if the intrinsic heart rate is rapidly decreasing, which increases the likelihood of a pacing interval expiring. For example, the rate drop threshold may require that the slope of the intrinsic heart rate falls 30 beats per minute within one minute. This rate drop threshold is a negative slope threshold corresponding to a relatively rapid decrease in heart rate. The drop threshold and required time interval or number of sensed event intervals for determining the slope compared to the drop threshold may be defined differently than the respective slope and threshold determined and used at blocks 324 and 325 for detecting a rapid rise in heart rate.

If the slope of the intrinsic heart rate change is greater than (e.g., less negative than) the drop threshold, delayed charging of the holding capacitor(s) continues at block 327. The heart rate may be increasing (a positive slope), stable (zero slope), or slowly decreasing (smaller negative slope than the drop threshold), such that there is a relatively low probability that a pacing interval will expire. If the slope is less than (more negative than) the drop threshold at block 329, indicating a rapid decrease in heart rate and an increased likelihood of a pacing interval expiring, control circuit 80 may switch to charging the holding capacitor(s) without delay at block 328.

It is to be understood that all or a part of the process of flow chart 320 may be combined with the techniques described above in conjunction with FIGS. 6 through 9C such that control circuit 80 may switch the control of capacitor charging in response to the slope of a heart rate change crossing a slope threshold, e.g., being greater than the positive, increasing slope threshold at block 325 and/or less than the negative, drop slope threshold at block 329 before other increased intrinsic heart rate detection criteria or decreased intrinsic heart rate detection criteria are met. When combined with the techniques for switching capacitor charging mode based on other increased intrinsic heart rate detection criteria and decreased intrinsic heart rate detection criteria, control circuit 80 may respond appropriately to both rapid and relatively slower changes in intrinsic heart rate by switching the capacitor charging mode in a manner that conserves battery energy of power source 98 when expiration of a pacing interval is less likely and maintains the holding capacitor charge in a ready state when a pacing interval expiration is relatively more likely.

Figure 12:
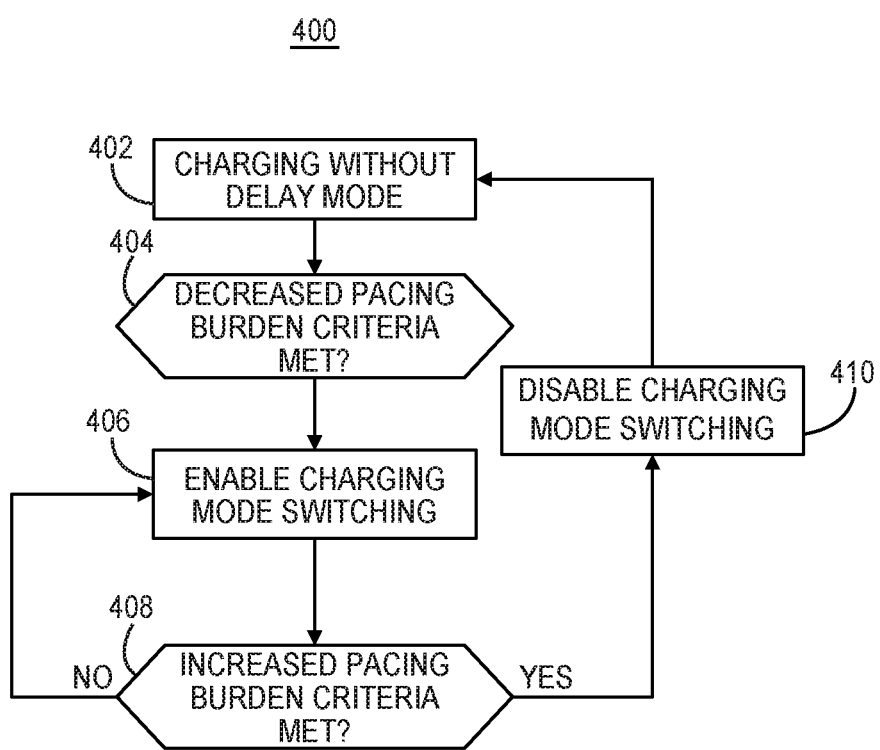
FIG. 12 is flow chart of a method for controlling capacitor charging for cardiac pacing according to another example.

FIG. 12 is flow chart 400 of a method for enabling and disabling the capacitor charging mode switching function based on detecting changes in pacing burden according to one example. ICD 14 may operate according to the techniques described above in conjunction with any of FIGS. 6 through 11 on a continuous basis. In other words, control circuit 80 may be enabled to automatically switch between a charging without delay mode and a delayed charging mode based on intrinsic heart rate criteria at any time of day or independent of other physiological conditions. In other examples, control circuit 80 may operate only in a default capacitor charging mode, e.g., charging without delay, with the function of switching between charging without delay and delayed charging modes disabled (turned off). The function of charging mode switching may be enabled (turned on) and disabled (turned off) by control circuit 80 in response to an actual or predicted change in pacing burden.

In FIG. 12, ICD 14 initially operates in a default capacitor charging mode at block 402. In the example shown, the default mode is charging without delay during each pacing interval to maintain the capacitor charge in a ready state for delivering a pacing pulse the next time a pacing interval expires. The functions of detecting a change in intrinsic heart rate based on predefined criteria and switching between capacitor charging modes may be disabled or turned off during this default charging mode.

At block 404, control circuit 80 may monitor one or more parameters for determining if decreased pacing burden criteria are satisfied. A decreased pacing burden may be determined or predicted based on pacing history, time of day, and/or other physiological signals received from sensors 90. In one example, decreased pacing burden criteria are met when the time of day is determined to be nighttime or a programmable time of day that the patient is normally resting, goes to bed or is asleep. In response to the time of day reaching the programmed "night" time, control circuit 80 may enable or turn on the function of switching capacitor charging mode at block 406. Enabling the function of automatic switching between charging modes does not necessarily mean that switching from one charging mode to the other occurs right away. Rather, after turning on the switching mode function, monitoring for detecting changes in intrinsic heart rate may be performed to control switching between the two charging modes. In order to actually switch from the charging without delay mode that is currently active to the delayed charging mode, increased intrinsic heart rate criteria need to be met, e.g., based on a sensed intrinsic event during at least one hysteresis interval as described above in conjunction with FIGS. 8C and 8D.

After enabling the function of charging mode switching at block 406, control circuit 80 may monitor one or more parameters for determining if increased pacing burden criteria are met at block 408. The switching function may be turned off or disabled again at block 410 if increased pacing burden criteria are met. In the illustrative example of enabling charging mode switching at block 406 in response to determining that the time of day is "night" at block 404, corresponding to an expected decrease in pacing demand, control circuit 80 may determine that increased pacing burden criteria are met at block 408 in response to the time of day reaching morning or a programmed time of day that the patient is expected to wake up or become active. In a given patient, the pacing burden may be expected to be higher during active daytime hours than during night time hours. The increased pacing burden criteria are met at block 408 based on the time of day and an expected higher pacing frequency during daytime hours. It is recognized that the time of day that is detected as meeting decreased pacing burden criteria and the time of day that is detected as meeting increased pacing burden criteria may be tailored according to a patient's individual habits and daily routine.

In other examples, the increased pacing burden criteria may be determined to be satisfied at block 408 based on an increase in the actual pacing burden determined as the number or percentage of delivered pacing pulses during a predetermined time period, e.g., over at least one hour or more. In response to the increased pacing burden criteria being met at block 408, control circuit 80 disables the function of charging mode switching at block 410. Control circuit 80 operates to control the therapy delivery circuit 84 to charge the holding capacitor(s) according to the default pacing mode, which may be the charging without delay pacing mode as indicated at block 402, without monitoring for intrinsic heart rate changes and without switching between charging modes.

Other criteria for detecting a decreased pacing burden at block 404 may include an actual pacing burden falling below a predetermined threshold. For example, the pacing burden may be determined as the number of pacing pulses, the percentage of pacing pulses delivered out all cardiac events, or the ratio of paced events to intrinsic sensed events during a predetermined time interval, e.g., one hour, two hours, four hours, eight hours, twelve hours, twenty-four hours, one week or other time interval. If the pacing burden falls below a pacing burden threshold, the decreased pacing burden criteria are met at block 404. To illustrate, if fewer than 10% of all events, sensed and paced, are delivered pacing pulses over the past twenty-four hours, control circuit 80 may enable charging mode switching at block 406 such that delayed capacitor charging may be performed when increased intrinsic heart rate criteria are met.

Other examples of criteria for determining that the decreased pacing burden criteria are met at block 404 may be based on a sensor signal received from sensors 90. For instance a decrease in patient activity or a decreased sensor indicated pacing rate as determined from an activity sensor signal or other indicator of decreased metabolic demand, such as decreased respiratory minute volume, may be an indicator of decreased pacing burden. Similarly, criteria for detecting an increased pacing burden may be satisfied at block 408 in response to detecting an increase in patient activity or sensor indicated rate determined from a patient activity sensor, such as an accelerometer or an impedance sensor used to track respiratory minute volume as an indication of increased metabolic demand.

Other physiological sensor signals correlated to the patient's hemodynamic function may be used to determine that decreased pacing burden criteria are met at block 404 and/or increased pacing burden criteria are met at block 408. For example a signal or metric derived from a pressure sensor, oxygen saturation sensor, impedance sensor, or other physiological sensor may be determined and compared to a threshold for determining a need for increased cardiac output. The increased pacing burden criteria may be satisfied based on a need to increase the cardiac output. For instance, blood pressure, tissue or blood oxygen saturation, or other parameter that is correlated to cardiac output may be determined by control circuit 80 from a sensor signal and compared to a threshold at block 408. If the parameter indicates that cardiac output is low, e.g., below a predetermined threshold, such that an increase in cardiac output is needed, increased pacing burden criteria may be determined to be satisfied at block 408, and charging mode switching may be disabled at block 410.

The decreased pacing burden criteria and the increased pacing burden criteria may be defined differently such that different criteria, which may include different parameters and/or different thresholds applied to respective parameters, are used to determine when to enable and disable the function of switching charging mode. For example, the time of day may be used to detect satisfaction of decreased pacing burden criteria for enabling capacitor charging mode switching while a sensor signal parameter, e.g., indicative of an increased metabolic demand or a need for increased cardiac output, may be used to detect that increased pacing burden criteria are met at block 408 for disabling charging mode switching at block 410.

After charging mode switching is enabled at block 406, control circuit 80 may operate according to any of the techniques described above for detecting an increased intrinsic heart rate and switching to delayed capacitor charging. After switching to delayed capacitor charging, control circuit may monitor for a decreased intrinsic heart rate and switch back to capacitor charging without delay as long as the switching function has not been disabled due to increased pacing burden criteria being met.

It is further contemplated that the default charging mode is the delayed charging mode rather than the charging without delay mode as shown in FIG. 12. The capacitor charging mode switching function may be enabled and/or disabled based on an actual or predicted pacing burden change crossing a pacing burden threshold. A patient receiving ICD 14 may be expected to seldom require pacing. In that case, control circuit 80 may control therapy delivery circuit 84 to delay capacitor charging until a charging delay interval or pacing interval expires without a sensed intrinsic event. A slow intrinsic heart rate that requires pacing may occur without switching to the charging without pacing mode as long as the charging mode switching function remains disabled. Control circuit 80 may monitor actual pacing burden based on the frequency of delivered pacing pulses, the time of day, and/or one or more physiological signals from sensors 90 for determining if increased pacing burden criteria are met, e.g. as described above in conjunction with block 408. In response to the increased pacing burden criteria being met, control circuit 80 may enable switching between capacitor charging modes. After capacitor charging mode switching is enabled, control circuit 80 monitors for intrinsic heart rate changes and may switch from delayed capacitor charging to charging without delay in response to decreased intrinsic heart rate criteria being met.

In some examples, after enabling the switching between charging modes, the switching function may never be disabled again. For example, upon initial implant, ICD 14 may operate according to a default capacitor charging mode, either charging with delay or delayed charging, with switching between the two modes disabled based on the anticipated pacing needs of the patient. Upon detecting that a change in pacing burden has occurred or is expected to occur, using any one or combination of the criteria described above, capacitor charging mode switching is enabled. After being enabled, control circuit 80 switches between the two charging modes based on detecting increased and decreased intrinsic heart rates according to predetermined criteria using any of the examples given herein. Capacitor charging mode switching may remain enabled without ever being automatically disabled by control circuit 80, e.g., for the remaining life of the ICD 14 or until manually reprogrammed by a user.

Figure 13:
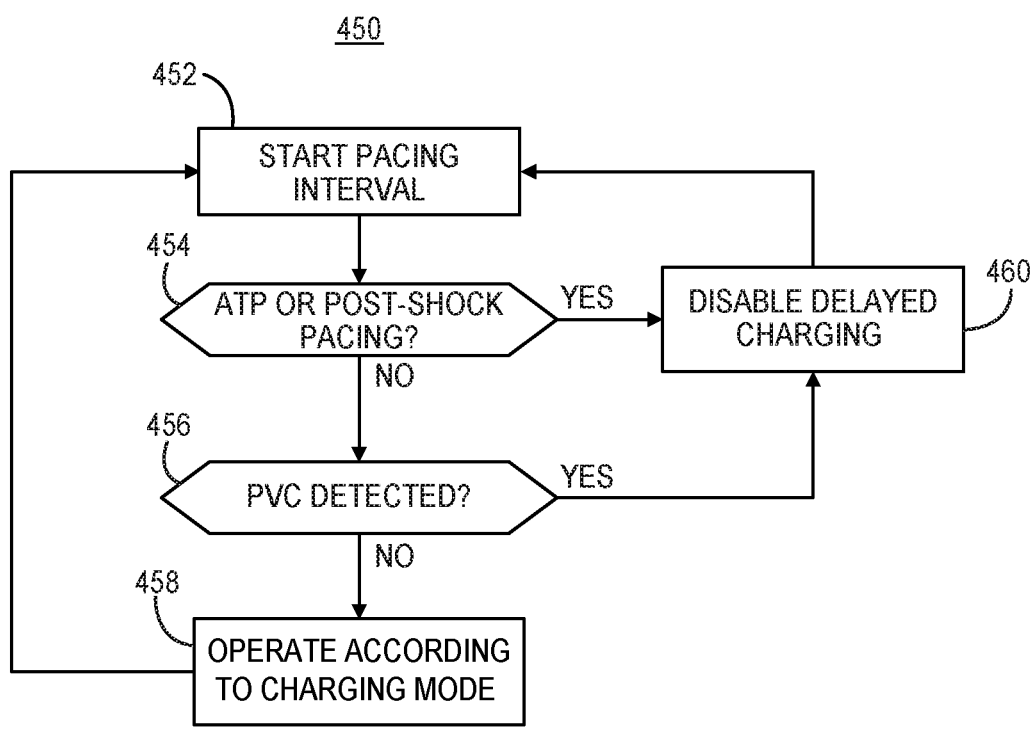
FIG. 13 is a flow chart of a method for controlling capacitor charging based on different pacing therapies according to one example.

FIG. 13 is a flow chart 450 of a method for controlling capacitor charging by ICD 14 based on different pacing therapies according to one example. Control circuit 80 may start a pacing interval at block 452 in response to a sensed event signal or a delivered electrical stimulation pulse or other determination of a need for a pacing therapy. In some cases, the delivered stimulation pulse may be a CV/DF shock pulse in which case the pacing interval may be post-shock pacing interval for preventing post-shock asystole. If the pacing interval is a post-shock pacing interval, as determined at block 454, the control circuit 80 may be configured to disable delayed capacitor charging at block 460 in anticipation of a potential critical need for pacing without delay. Control circuit 80 may be configured to control the therapy delivery circuit 84 to deliver post-shock pacing by charging the selected LV or HV holding capacitor(s) to the pacing voltage amplitude during each post-shock pacing interval, e.g., starting at the beginning of each pacing interval and in some instances throughout the pacing interval as needed to maintain the holding capacitor charge at the programmed pacing voltage amplitude.

In other cases, the pacing interval started at block 452 may be started in response to a sensed event signal at the time of a tachyarrhythmia detection. In this case, the pacing interval may be an ATP interval set to control the delivery of a series of ATP pulses. If the pacing interval is an ATP pacing interval, control circuit 80 may be configured to disable delayed charging of the holding capacitor at block 460. Capacitor charging is performed during each ATP pacing interval without delay to promote accurate timing of ATP pacing pulses and successful tachyarrhythmia termination.

At other times, the pacing interval started at block 452 may be a bradycardia pacing interval, e.g., a VVI pacing interval, started in response to a delivered bradycardia pacing pulse or R-wave sensed event signal. If the pacing interval was started as a bradycardia pacing interval ("no" branch of block 454) and the precipitating event is a sensed event signal that is detected as a premature ventricular contraction (PVC) by the control circuit 80, the control circuit 80 may disable delayed capacitor charging at block 460 for one cycle. Capacitor charging may be performed during the pacing interval started in response to a sensed event identified as a PVC without delay as needed to top-off the capacitor charge to the pacing voltage amplitude. In this way, the therapy delivery circuit 84 is ready to deliver a pacing pulse in anticipation of a long, compensatory pause following the PVC. Control circuit 80 may be configured to detect a sensed R-wave as a PVC based on the sensed event interval (RR interval) since a most recent preceding ventricular event (paced or sensed) and/or whether or not an atrial P-wave was sensed prior to the sensed R-wave during the RR interval ending on the sensed R-wave. For example, an R-wave sensed event signal that is received at an RRI that is less than a PVC detection threshold interval may be detected as a PVC at block 406.

In other examples, PVCs may be ignored for the purposes of controlling changes in the capacitor charging state. For example, a short sensed event interval determined to end on a sensed event signal identified as a PVC may be ignored in detecting an increased intrinsic heart rate. A long sensed event interval (the compensatory pause) following a sensed event signal identified as a PVC may be ignored in detecting a decreased intrinsic heart rate. In this way, a PVC or a run of PVCs will not alter the capacitor charging state by causing capacitor charging mode switching. If the control circuit 80 is presently operating to charge the holding capacitor(s) used for generating pacing pulses without delay, sensed event intervals immediately preceding and immediately following a PVC are ignored for the purposes of detecting a change in intrinsic heart rate. No change to the capacitor charging without delay is made. Likewise, if the control circuit 80 is presently operating in the delayed charging mode, the sensed event interval immediately preceding a sensed event identified as a PVC and the sensed event interval immediately following the PVC are ignored for the purposes of detecting a change in the intrinsic heart rate.

If the pacing interval started at block 452 is not an ATP pacing interval or a post-shock pacing interval and is not started in response to a sensed event signal that is detected as a PVC ("no" branch of block 456), the control circuit 80 may operate according to the current capacitor charging control mode at block 458. If the control circuit 80 is operating to delay capacitor charging until the expiration of a capacitor charging delay interval or until expiration of a pacing interval, the capacitor charging is withheld during the pacing interval that was started at block 452 according to the delayed charging mode. Capacitor charging is delayed until the expiration of the pacing interval or a capacitor charging delay interval as described in conjunction with FIGS. 9a-9c. If the control circuit 80 has recently detected a decreased intrinsic heart rate and is operating to charge without delay, capacitor charging may be performed without delay, e.g., at the beginning and/or throughout, the pacing interval started at block 452 as needed to maintain the holding capacitor in a ready state for pacing pulse delivery.

Control circuit 80 may be configured to enable delayed capacitor charging only during selected pacing therapies, e.g., during VVI pacing, so that pacing pulse delivery is not delayed during other pacing therapies such as post-shock pacing and ATP when pacing pulse timing may be critical. Depending on the types of electrical stimulation therapies that the ICD 14 or other IMD implementing the techniques disclosed herein is capable of, the control circuit 80 may be configured to disable delayed capacitor charging for one or more therapies and enable delayed capacitor charging for one or more therapies.

Figure 14:
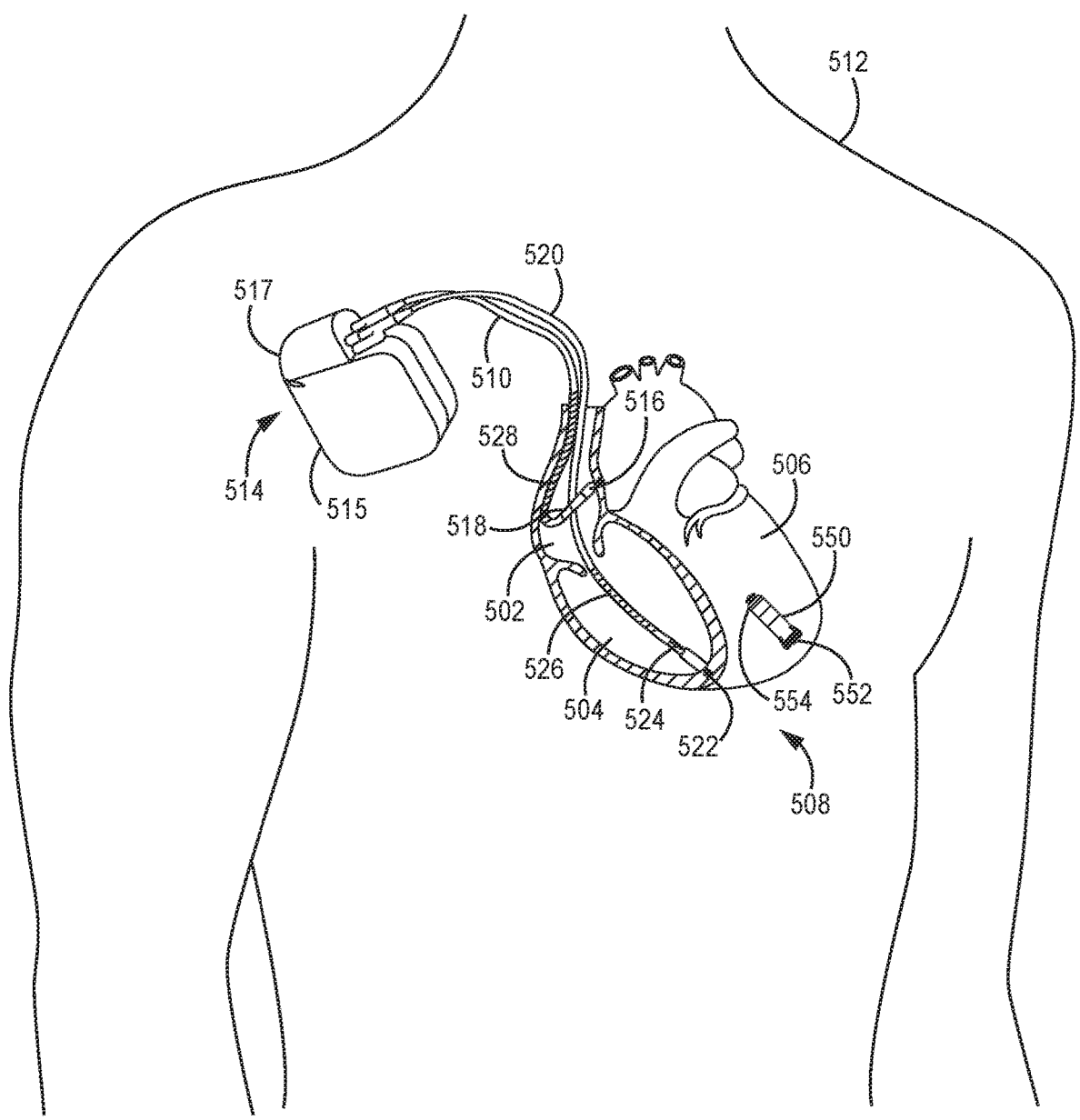
FIG. 14 is a diagram of another IMD system that may be configured to control capacitor charging for pacing therapy delivery using the techniques disclosed herein.

FIG. 14 is a diagram of an IMD system 500 that may be configured to control delayed capacitor charging for pacing therapy delivery according to another example.

IMD system 500 may include ICD 514 and intra-cardiac pacemaker 550. ICD 514 is shown coupled to transvenous leads 510 and 520 in communication with the right atrium (RA) 502 and right ventricle (RV) 504, respectively, of heart 508. ICD 514 is shown as a dual-chamber pacemaker and cardioverter/defibrillator configured to sense cardiac signals and deliver electrical stimulation pulses in RA 502 and RV 504. ICD 514 includes a housing 515 enclosing electronic circuitry, e.g., a sensing circuit, therapy delivery circuit, control circuit, memory, telemetry circuit, other optional sensors, and a power source as generally described in conjunction with FIG. 3 above. ICD 514 is shown implanted in a right pectoral position in FIG. 14, however it is recognized that ICD 514 may be implanted in other locations, e.g., in a left pectoral position, particularly when ICD 514 includes cardioversion and defibrillation capabilities using housing 515 as an active electrode.

ICD 514 has a connector assembly 517 for receiving proximal connectors of RA lead 510 and RV lead 520. RA lead 510 may carry a distal tip electrode 512 and ring electrode 514 for sensing atrial signals, e.g., P-waves attendant to atrial depolarization, and delivering RA pacing pulses. RV lead 520 may carry pacing and sensing electrodes 522 and 524 for sensing ventricular signals, e.g., R-waves attendant to RV depolarization, and for delivering RV pacing pulses. RV lead 520 may also carry RV defibrillation electrode 526 and a superior vena cava (SVC) defibrillation electrode 528. Defibrillation electrodes 526 and 528 are shown as coil electrodes spaced apart proximally from the distal pacing and sensing electrodes 522 and 524 and may be used for delivering high voltage CV/DF shock pulses.

ICD 514 may be configured to provide dual chamber pacing in RA 502 and RV 504. In some examples, IMD system 500 may include an intracardiac pacemaker 550 positioned in left ventricle 506 for sensing left ventricular signals, e.g., R-waves attendant to left ventricular depolarizations, and for delivering pacing pulses to left ventricle 506. IMD system 500 may be configured to deliver multi-chamber pacing therapies such as cardiac resynchronization therapy (CRT). Intra-cardiac pacemaker 550 may be configured to deliver left ventricular pacing pulses to synchronize left ventricular contraction with RA and RV contractions to promote a normal atrio-ventricular interval and coordinated ventricular contractions. ICD 514 may be configured to deliver RA pacing pulses and RV pacing pulses as needed to prevent the heart rate from falling below a programmed lower pacing rate. In some patients, occasional atrial bradycardia or AV conduction block may cause slowing of the intrinsic rate requiring pacing of the RA 502 and/or RV 504. During CRT, however, left ventricular pacing by intra-cardiac pacemaker 550 may occur on a beat-by-beat basis, whether RA 502 and RV 504 are being paced or sensed, for promoting optimal heart chamber synchrony.

Intra-cardiac pacemaker 500 may include housing based electrodes 552 and 554 for sensing cardiac signals in the left ventricle 506 and delivering left ventricular pacing pulses. Pacemaker 500 may include a sensing circuit and therapy delivery circuit that includes at least one pacing channel in a low voltage therapy circuit including a low voltage charging circuit, a holding capacitor, and an output capacitor, e.g., as generally described in conjunction with FIG. 5, for generating and delivering pacing pulses to the left ventricle. In some examples, intra-cardiac pacemaker 550 includes a control circuit configured to perform the methods disclosed herein in conjunction with the accompanying flow charts for controlling holding capacitor charging. For example, the control circuit of intra-cardiac pacemaker 550 may switch between delayed holding capacitor charging following detection of an increased intrinsic heart rate and charging without delay during a pacing interval following detection of a decreased intrinsic heart rate, respectively, as described above. Some patients may require sustained or prolonged episodes of left ventricular pacing in order to promote heart chamber synchrony. In this case, intra-cardiac pacemaker 550 may be configured to perform capacitor charging during each pacing interval without delay.

For example, patient 512 may be dependent on LV pacing by intra-cardiac pacemaker 550 for promoting heart chamber synchrony, but RA pacing and RV pacing may be seldom required. In this situation, ICD 514 may be configured to switch between delayed capacitor charging and charging without delay modes in one or both of the RA and RV pacing channels of ICD 514 to conserve battery charge. For example, when increased intrinsic rate criteria are satisfied by sensed events (P-waves) in the RA and/or sensed events (R-waves) in the RV, the holding capacitors corresponding to the RA pacing channel and the RV pacing channel may be charged according to the delayed charging mode.

ICD 514 may include at least two pacing channels of a low voltage therapy circuit, e.g., any two of channels 342, 344 and 346 of low voltage therapy module 85 as shown in FIG. 5, for providing pacing to RA 502 and RV 504. For example, RA electrodes 516 and 518 may be coupled to pacing channel 346 of low voltage therapy circuit 85 for delivering RA pacing pulses. RV electrode 522 and 524 may be coupled to pacing channel 344 of low voltage therapy circuit 85 for delivering RV pacing pulses. The control circuit of ICD 514 may be configured to delay capacitor charging in one or both of the RA pacing channel and the RV pacing channel based on increased intrinsic rate criteria being satisfied in the respective heart chamber.

For instance, with reference to the low voltage therapy circuit 85 of FIG. 5, charging of low voltage holding capacitor 358 may be delayed in response to detecting an increased intrinsic atrial rate based on the rate of sensed P-waves by the sensing circuit of ICD 514. A hysteresis interval may be set after each sensed P-wave for detecting an increased intrinsic atrial rate in response to a threshold number of cardiac cycles in which a sensed P-wave occurs during the hysteresis interval. ICD 514 may switch to charging the holding capacitor 358 of the pacing channel 346 being used as the atrial pacing channel to the charging without delay mode in response to detecting a decreased intrinsic atrial rate based on one or more expired atrial pacing intervals.

The control circuit of ICD 514 may set an AV pacing interval following each atrial pacing pulse and sensed P-wave in RA 502 for controlling the timing of pacing pulses delivered to RV 504 by pacing channel 344 used as an RV pacing channel coupled to electrodes 522 and 524. Additionally or alternatively, the control circuit of ICD 514 may set a VV pacing interval following each RV pacing pulse and each R-wave sensed in RV 504 for controlling the timing of RV pacing pulses delivered by pacing channel 344. The control circuit of ICD 514 may delay charging of low voltage holding capacitor 356 until after a capacitor charging delay interval or after expiration of an expired AV or VV pacing interval in response to detecting an increased intrinsic ventricular rate based on a threshold number of cardiac cycles having an R-wave sensed in the RV 504 during a hysteresis interval. The control circuit of ICD 514 may switch to charging without delay in response to the expiration of a threshold number of pacing intervals and/or charging delay intervals. In some examples, control of capacitor charging using delayed charging after detecting an increased intrinsic rate is used only for controlling charging during AA or VV pacing intervals. Delayed capacitor charging may not be used for controlling capacitor charging associated with AV pacing intervals since AV pacing intervals are relatively shorter than AA and VV pacing intervals and a ventricular pacing pulse delivered at a long AV interval due to delayed capacitor charging may be undesirable.

In other examples, a pacemaker or ICD incorporating the techniques disclosed herein may be a single chamber pacemaker or ICD coupled to a single transvenous lead or a multi-chamber pacemaker or ICD coupled to three transvenous leads including a RA lead, RV lead and a coronary sinus lead for sensing and stimulating in RA 502, RV 504 and LV 506, respectively. In other examples of an IMD system performing the techniques disclosed herein, the intra-cardiac pacemaker 550 may be included in an implantable system with ICD 14 and extra-cardiovascular lead 16 shown in FIG. 1A. Intra-cardiac pacemaker 550 may be placed in any atrial or ventricular chamber and control capacitor charging using the methods described above for delaying capacitor charging in response to increased intrinsic heart rate criteria being satisfied.

Figure 15:
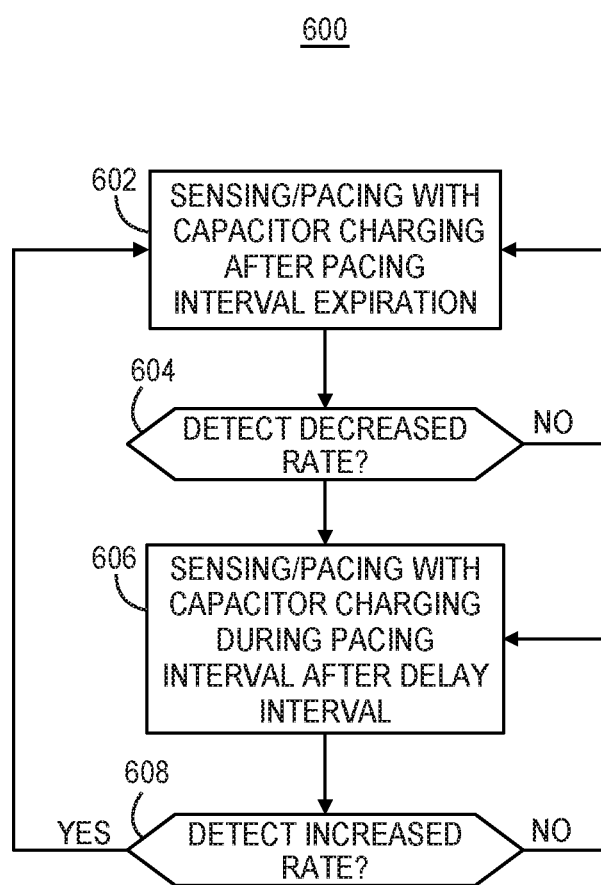
FIG. 15 is a flow chart of a method for controlling holding capacitor charging according to yet another example.

FIG. 15 is a flow chart 600 of a method for controlling holding capacitor charging according to yet another example. Control circuit 80 may control the therapy delivery circuit 84 to charge the holding capacitor(s) used for pacing pulse delivery in response to a pacing interval expiring at block 602 during a delayed capacitor charging mode. Capacitor charging is withheld for the pacing interval by delaying charging until after the pacing interval expires.

If decreased intrinsic heart rate criteria are satisfied at block 604, e.g., using any of the decreased intrinsic heart rate criteria described above such as a threshold number of expired pacing intervals or a slope of the heart rate change being less than (more negative than) a drop threshold, control circuit 80 may switch to charging the holding capacitor(s) during the pacing interval but after expiration of the capacitor charging delay interval at block 606. In this way, charging is only performed when the intrinsic heart rate is slower than the rate corresponding to the capacitor charging delay interval. A sensed event during the capacitor charging delay interval causes pacing pulse inhibition and charging is withheld. When increased intrinsic heart rate detection criteria are met, as determined at block 608, control circuit 80 switches back to delayed charging at block 602 and withholds capacitor charging until a pacing interval expires. Charging occurs when the heart rate is slower than the pacing rate.

This method of charging only when the intrinsic rate is less than the rate corresponding to capacitor charging delay interval may be used in an IMD and electrode system having relatively low pacing capture thresholds. For example, intra-cardiac pacemaker 550 having housing-based electrodes in close proximity or in intimate contact with the endocardium or ICD 514 having transvenous leads with endocardial electrodes are expected to have relatively low pacing capture thresholds. The time required to charge a holding capacitor to the programmed pacing voltage amplitude may be relatively short such that charging may occur after a charging delay interval, even when the likelihood of a pacing interval expiring is increased based on decreased intrinsic rate criteria being met. When the likelihood of a pacing interval expiring is relatively lower, based on increased intrinsic heart rate criteria being met, charging may occur after the pacing interval expires without resulting in a clinically significant delay to pacing pulse delivery. In this example, charging after the capacitor charging delay interval may be considered the "charging without delay mode" since charging is still performed during the pacing interval. Charging after the pacing interval expires may be considered the "delayed charging mode" since charging is withheld and delayed until after the pacing interval expires.

Methods described in conjunction with flow diagrams presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented by processing circuitry hardware as execution of one or more software modules, which may be executed by themselves or in combination with other software.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Thus, IMD systems and methods for controlling holding capacitor charging for pacing therapy delivery have been presented in the foregoing description with reference to specific embodiments. In other examples, various methods described herein may include steps performed in a different order or different combination than the illustrative examples shown and described herein. It is appreciated that various modifications to the referenced embodiments may be made without departing from the scope of the disclosure and the following claims.

The invention claimed is:

1. A method performed by a medical device, the method comprising:
sensing a cardiac electrical signal by a sensing circuit of the medical device;
delivering a pacing pulse by a therapy delivery circuit of the medical device;
starting by the medical device a first pacing interval corresponding to a pacing rate in response to the delivered pacing pulse;
charging a holding capacitor by the therapy delivery circuit during the first pacing interval according to a first charging mode for generating pacing pulses;
detecting by the medical device an increased intrinsic heart rate from the sensed cardiac electrical signal that is at least a threshold rate faster than the pacing rate;
in response to detecting the increased intrinsic heart rate, switching by the therapy delivery circuit from the first charging mode to a second charging mode for generating the pacing pulses;
sensing a first intrinsic cardiac event from the cardiac electrical signal;
during the second charging mode, starting a second pacing interval corresponding to the pacing rate in response to the first intrinsic cardiac event sensed from the cardiac electrical signal; and
delaying by the medical device charging of the holding capacitor to a pacing voltage amplitude for at least a portion of the second pacing interval according to the second charging mode.

2. The method of claim 1, wherein detecting the increased intrinsic heart rate comprises detecting at least one sensed cardiac event from the cardiac electrical signal at a hysteresis rate that is greater than the pacing rate.

3. The method of claim 1, further comprising:
starting a capacitor charging delay interval in response to the first sensed intrinsic cardiac event;
delaying charging of the holding capacitor until expiration of the capacitor charging delay interval; and
charging the holding capacitor in response to expiration of the capacitor charging delay interval.

4. The method of claim 3, further comprising:
terminating the capacitor charging in response to a second sensed intrinsic cardiac event during the second pacing interval and after the capacitor charging delay interval expiring.

5. The method of claim 4, further comprising:
detecting a second intrinsic cardiac event during the capacitor charging delay interval; and
restarting the capacitor charging delay interval without charging the holding capacitor in response to detecting the second intrinsic cardiac event during the capacitor charging delay interval.

6. The method of claim 4, further comprising
determining a capacitor charging time; and
setting the capacitor charging delay interval based on a difference between the second pacing interval and the capacitor charging time.

7. The method of claim 1, further comprising:
detecting the increased intrinsic heart rate in response to a predetermined number of consecutive intrinsic cardiac events sensed from the cardiac electrical signal by the sensing circuit;
starting a capacitor charging delay interval in response to detecting the increased intrinsic heart rate; and
delaying charging of the holding capacitor according to the second charging mode by delaying charging of the holding capacitor until expiration of the capacitor charging delay interval.

8. The method of claim 1, further comprising:
starting a hysteresis interval;
detecting the increased intrinsic heart rate in response to detecting the first intrinsic cardiac event during the hysteresis interval;
starting a capacitor charging delay interval in response to detecting the increased intrinsic heart rate; and
delaying charging of the holding capacitor according to the second charging mode by delaying charging of the holding capacitor until expiration of the capacitor charging delay interval.

9. The method of claim 1, further comprising:
detecting a decreased intrinsic heart rate;
disabling delaying of the capacitor charging in response to detecting the decreased intrinsic heart rate.

10. The method of claim 9, further comprising:
delaying charging of the holding capacitor by setting a capacitor charging delay interval in response to the first intrinsic cardiac event, the capacitor charging delay interval less than the second pacing interval; and
detecting the decreased intrinsic heart rate in response to a predetermined number of capacitor charging delay intervals expiring without sensing a cardiac event from the cardiac electrical signal during the predetermined number of capacitor charging delay intervals.

11. The method of claim 9, wherein:
detecting the decreased intrinsic heart rate comprises detecting the decreased intrinsic heart rate in response to decreased intrinsic heart rate criteria being satisfied;
determining a rate of decrease of the decreased intrinsic heart rate; and
adjusting the decreased intrinsic heart rate criteria based on the rate of decrease.

12. The method of claim 1, further comprising:
setting the first pacing interval corresponding to a first pacing therapy;
setting a third pacing interval corresponding to a second pacing therapy different than the first pacing therapy;
disabling delaying of the charging of the holding capacitor in response to setting the third pacing interval.

13. The method of claim 1, further comprising:
detecting a premature ventricular contraction; and
disabling delaying of the charging of the holding capacitor in response to detecting the premature ventricular contraction.

14. The method of claim 1, further comprising:
detecting a premature ventricular contraction from the cardiac electrical signal;
wherein detecting the increased intrinsic heart rate comprises ignoring the premature ventricular contraction.

15. The method of claim 1, further comprising:
detecting the increased intrinsic heart rate in response to increased intrinsic heart rate criteria being satisfied;
determining a rate of increase of the increased intrinsic heart rate; and
adjusting the increased intrinsic heart rate criteria based on the rate of increase.

16. The method of claim 1, further comprising:
controlling holding capacitor charging according to only one of the first charging mode or the second charging mode with switching between the first and second charging modes disabled;
determining an actual pacing burden over a predetermined time interval;
comparing the actual pacing burden to a pacing burden threshold; and
enabling switching between the first charging mode and the second charging mode in response to the actual pacing burden crossing the pacing burden threshold.

17. The method of claim 1, further comprising;
monitoring a sensor signal correlated to a patient condition;
detecting a change in expected pacing burden based on the sensor signal; and
in response to detecting a change in the expected pacing burden, enabling switching between the first charging mode and the second charging mode.

18. The method of claim 1, further comprising a sensor configured to produce a signal correlated to a patient condition;
monitoring a sensor signal that is correlated to a patient condition:
detecting an expected increase in pacing burden based on the sensor signal; and
switching from the second charging mode to the first charging mode in response to detecting the expected increase in pacing burden.

19. The method of claim 1, further comprising:
determining a slope of a change in rate of intrinsic cardiac events sensed from the cardiac electrical signal;
comparing the slope to a slope threshold; and
switching between the first and second charging modes in response to the slope crossing the slope threshold.

20. The method of claim 1, wherein the control circuit is further configured to:
enable the switching between the first charging mode and the second charging mode based on a time of day.

21. The method of claim 1, wherein:
charging the holding capacitor comprises charging a high voltage holding capacitor that is chargeable to a cardioversion/defibrillation shock voltage amplitude to the pacing voltage amplitude for delivering the pacing pulse; and
delaying the charging comprises delaying charging of the high voltage holding capacitor in response to detecting the increased intrinsic heart rate.

22. The method of claim 1, wherein:
charging the holding capacitor comprises charging at least two low voltage holding capacitors to the pacing voltage amplitude for delivering the pacing pulse; and
delaying the charging comprises delaying charging of the at least two low voltage holding capacitors in response to detecting the increased intrinsic heart rate.

23. The method of claim 1, further comprising:
delaying charging of the holding capacitor according to the second charging mode by delaying a comparison of a charge of the holding capacitor to the pacing voltage amplitude at a start of the second pacing interval;
detecting a decreased intrinsic heart rate;
switching from the second charging mode back to the first charging mode in response to detecting the decreased intrinsic heart rate;
starting a third pacing interval in response to a second intrinsic cardiac event sensed from the cardiac electrical signal; and
charging the holding capacitor according to the first charging mode during the third pacing interval by:
comparing a charge of the holding capacitor to a pacing voltage amplitude at a start of the third pacing interval, and
charging the holding capacitor in response to the holding capacitor voltage being less than the pacing voltage amplitude.

24. The method of claim 1, further comprising:
starting a capacitor charging delay interval;
delaying charging of the holding capacitor according to the second charging mode by withholding a comparison of a charge of the holding capacitor to the pacing voltage amplitude until the capacitor charging delay interval expires;
detecting a decreased intrinsic heart rate;
switching from the second charging mode back the first charging mode in response to detecting the decreased intrinsic heart rate;
starting a third pacing interval in response to a second intrinsic cardiac event sensed from the cardiac electrical signal; and
charging the holding capacitor according to the first charging mode during the third pacing interval by:
comparing a charge of the holding capacitor to a pacing voltage amplitude throughout the third pacing interval, and
charging the holding capacitor in response to the holding capacitor voltage being less than the pacing voltage amplitude.

25. The method of claim 1, further comprising:
charging the holding capacitor during the first pacing interval after a charging delay interval; and
in response to detecting the increased intrinsic heart rate, delaying charging of the holding capacitor until the second pacing interval expires according to the second charging mode.

* * * * *